United States Patent
Pandey et al.

(10) Patent No.: US 8,562,944 B2
(45) Date of Patent: Oct. 22, 2013

(54) PAA NANOPARTICLES FOR ENHANCEMENT OF TUMOR IMAGING

(75) Inventors: Ravindra K. Pandey, Williamsville, NY (US); Raoul Kopelman, Ann Arbor, MI (US); Anurag Gupta, Hamburg, NY (US); Munawwar Sajjad, Clarence Center, NY (US)

(73) Assignees: Health Research, Inc., Buffalo, NY (US); The Research Foundation of State University of NY, Amherst, NY (US); Regents of the University of Michigan, Ann Arbor, MI (US)

( * ) Notice: Subject to any disclaimer, the term of this patent is extended or adjusted under 35 U.S.C. 154(b) by 10 days.

(21) Appl. No.: 12/909,573

(22) Filed: Oct. 21, 2010

(65) Prior Publication Data
US 2011/0091373 A1   Apr. 21, 2011

Related U.S. Application Data

(60) Provisional application No. 61/279,522, filed on Oct. 21, 2009.

(51) Int. Cl.
*A61K 51/00* (2006.01)
*A61K 49/06* (2006.01)
*A61K 49/00* (2006.01)
*C07D 487/22* (2006.01)
*B82Y 5/00* (2011.01)

(52) U.S. Cl.
USPC ........... 424/1.11; 424/9.3; 424/9.61; 424/9.1; 977/930; 977/773; 977/927; 540/145

(58) Field of Classification Search
None
See application file for complete search history.

(56) References Cited

U.S. PATENT DOCUMENTS

2005/0196343 A1*  9/2005  Reddy et al. ............... 424/9.322

FOREIGN PATENT DOCUMENTS

WO    WO2009105209    *  8/2009

* cited by examiner

*Primary Examiner* — Suzanne Ziska
*Assistant Examiner* — Thurman Wheeler
(74) *Attorney, Agent, or Firm* — Michael L. Dunn

(57) ABSTRACT

A composition comprising PAA nanoparticles containing a post loaded tetrapyrollic photosensitizer and an imaging agent and methods for making and using same.

7 Claims, 23 Drawing Sheets

PAA NANOPARTICLES FOR ENHANCEMENT OF TUMOR IMAGING

CROSS-REFERENCE TO RELATED APPLICATIONS

This application claims the benefit under 35 U.S.C. §119(e) of U.S. Provisional Application No. 61/279,522, filed Oct. 21, 2009.

STATEMENT REGARDING FEDERALLY SPONSORED RESEARCH OR DEVELOPMENT

This invention was made with government support under Grant Numbers CA19358 and CA114053 awarded by the National Institute of Health. The government has certain rights in the invention.

BACKGROUND OF THE INVENTION

Therapeutic and Diagnostic NP Platforms and Nanovectors.

Nanoscience is being developed in conjunction with advanced medical science for further precision in diagnosis and treatment. Multidisciplinary biomedical scientific teams including biologists, physicians, mathematicians, engineers and clinicians are working to gather information about the physical properties of intracellular structures upon which biology's molecular machines are built. A new emphasis is being given to moving medical science from laboratory to the bedside and the community. This platform development program brings together an outstanding laboratory that is pioneering biomedical applications of PAA nanovectors (Kopelman), together with an innovative porphyrin chemistry and a world-class PDT group at RPCI that is highly experienced in the high volume screening and in vitro/in vivo evaluation of novel compounds, and in developing new therapies from the test tube to FDA approval for clinical use. Although nanoplatforms and nanovectors (i.e. a nanoplatform that delivers a therapeutic or imaging agent) for biomedical applications are still evolving, they show enormous promise for cancer diagnosis and therapy. The approach has been the subject of several recent reviews2 Therapeutic examples include NP containing PDT agents, folate receptor-targeted, boron containing dendrimers for neutron capture and NP-directed thermal therapy. Recently, we have evaluated the therapeutic and imaging potential of encapsulated, post-loaded and covalently linked photosensitizer-NPs. In PAA NP the post-loading efficiency showed enhanced in vitro/in vivo therapeutic and imaging potential. PAA NP have core matrixes that can readily incorporate molecular or small NP payloads, and can be prepared in 10-150 nm sizes, with good control of size distributions. The surfaces of NPs can be readily functionalized, to permit attachment of targeting ligands, and both are stable to singlet oxygen (1O2) produced during PDT. PAA-NP have the advantages of (1) A relatively large knowledge base on cancer imaging, PDT, chemical sensing, stability and biodegradation. (2) No known in-vivo toxicity. (3) Long plasma circulation time without surface modification (see Preliminary Data), but with biodegradation and bioelimination rates controllable via the type and amount of selective cross-linking (introduced during polymerization inside reverse micelles). (4) Scale-up to 400 g material has been demonstrated, as well as storage stability over extended periods. Limitations include relative difficulty in incorporating hydrophobic compounds (although we have accomplished this), leaching of small hydrophilic components unless they are "anchored", and unknown limitation on bulk tumor permeability because of hydrogel swelling.

PDT and Cancer Therapy.

The major challenge of cancer therapy is preferential destruction of malignant cells with sparing of the normal tissue. Critical for successful eradication of malignant disease are early detection and selective ablation of the malignancy. PDT is a clinically effective and still evolving locally selective therapy for cancers. The utility of PDT has been demonstrated with various photosensitizers for multiple types of disease. It is FDA approved for early and late stage lung cancer, obstructive esophageal cancer, high-grade dysplasia associated with Barrett's esophagus, age-related macular degeneration and actinic keratoses. PDT employs tumor localizing PSs that produce reactive $1O_2$ upon absorption of light which is responsible for the destruction of the tumor. Subsequent oxidation-reduction reactions also can produce superoxide anions, hydrogen peroxide and hydroxyl radicals which contribute to tumor ablation4. Photosensitizers have been designed which localize relatively specifically to certain subcellular structures such as mitochondria, which are highly sensitive targets5. On the tumor tissue level, direct photodynamic tumor cell kill, destruction of the tumor supporting vasculature and possibly activation of the innate and adaptive anti-tumor immune system interact to destroy the malignant tissue6. The preferential killing of the targeted cells (e.g. tumor), rather than adjacent normal tissues, is essential for PDT, and the preferential target damage achieved in clinical applications is a major driving force behind the use of the modality. The success of PDT relies on development of tumor-avid molecules that are preferentially retained in malignant cells but cleared from normal tissues. Clinical PDT initially was developed at Roswell Park Cancer Institute (RPCI), and we have one of the world's largest basic and clinical research programs. The RPCI group developed Photofrin®, the first generation FDA approved hematoporphyrin-based compound. Subsequently, our group has investigated structure activity relationships for tumor selectivity and photosensitizing efficacy, and used the information to design new PSs with high selectivity and desirable pharmacokinetics. Although the mechanism of porphyrin retention by tumors in not well understood, the balance between lipophilicity and hydrophilicity is recognized as an important factor7 In our efforts to develop effective photosensitizers with the required photophysical characteristics, we used chlorophyll-a and bacteriochlorophyll-a as the substrates. Extensive QSAR studies on a series of the alkyl ether derivatives of pyropheophorbide-a (660 nm) led to selection of the best candidate, HPPH (hexyl ether derivative) 8,9, now in promising Phase II clinical trials. Our PS development now extends to purpurinimide (700 nm) and bacteriopurpurinimde (780-800 nm) series with high 102 producing capability 10-13 Long wavelength absorption is important for treating large deep-seated tumors, because longer wavelength light increases penetration and minimizes the number of optical fibers needed for light delivery within the tumor Advantages of Longer Wavelength Photosensitizers (700-800 nm) for Phototherapy Over HPPH:

The penetration of light through tissue increases as its wavelength increases between 630 and 800 nm. Once light has penetrated tissue more than 2-3 mm it becomes fully diffuse (i.e. non-directional). In diffusion theory, the probability that a photon will penetrate a given distance into tissue is governed by the probability per unit path. The intrinsic absorption of most tissues is dominated by hemoglobin and deoxyhemoglobin, with the strong peaks of the absorption bands at wavelengths shorter than 630 nm. The tails of these bands extend beyond 630 nm and grow weaker with increasing wavelength. Thus the probability of a photon being absorbed by endogenous chromophores decreases with increasing wavelength from 630-800 nm and the scattering also decreases with wavelength14 resulting in the very large increase in light penetration at ~600 to 800 nm.

PDT and Nanoparticle Platforms

Photosensitizers have several very desirable properties as therapeutic agents deliverable by NP: (1) Only a very small fraction of administered targeted drug makes it to tumor sites and the remainder can cause systemic toxicity. However, PDT provides dual selectivity in that the PS is inactive in the absence of light and is innocuous without photoactivation. Thus the PS contained by the NP can be locally activated at the site of disease. (2) PDT effects are due to production of $1O_2$, which can readily diffuse from the pores of the NP (see Preliminary Data). Thus, in contrast to chemotherapeutic agents, release of encapsulated drug from the NP, is not necessary. Instead, stable NP with long plasma residence times can be used, which increases the amount of drug delivered to the tumors. (3) PDT is effective regardless of the intracellular location of the PS. While mitochondria are a principal target of $1O_2$, PS incorporated in lysosomes are also active the photodynamic process causes rupture of the lysosomes with release of proteolytic enzymes and redistribution of the PS within the cytoplasm. NP platforms also provide significant advantages for PDT: (1) High levels of imaging agents can be combined with the PS in the NP permitting a "see and treat" approach, with fluorescence imageguided placement of optical fibers to direct the photoactivating light to large or subsurface tumors, or to early non clinically evident disease. (2) It is possible to add targeting moieties, such as cRGD or F3 peptide to the NP so as to increase the selective delivery of the PS. (3) The NP can carry large numbers of PS, and their surface can be modified to provide the desired hydrophilicity for optimal plasma pharmacokinetics. Thus, they can deliver high levels of PS to tumors, reducing the amount of light necessary for tumor cure.

Molecular Targeting.

F3/Nucleolin Targeting

F3 peptide is a 31-amino acid synthetic peptide derived from a fragment of the nuclear protein, high mobility group protein 2 (HMGN2)15. HMGN2 is a highly conserved nucleosomal protein thought to be involved in unfolding higher-order chromatin structure and facilitating the transcriptional activation of mammalian genes 62 when injected i.v., F3 peptide internalizes and accumulates in the nuclei of HL-60 cells and human MDA-MB-35 breast cancer cells. Tissue and cellular localization of F3 peptide indicated that it homes selectively to tumor blood vessels and tumor cells and has the remarkable property of being able to carry a payload into the cytoplasm and nucleus of the target cells. Furthermore, NPs with surface attached F3 behave similarly, attaching selectively to nucleolin expressing cells, and then channeled towards the cell nucleus. Recent literature shows that the F3 peptide binds to cell surface-expressed nucleolin on the target cells. Although primarily known as a nuclear and cytoplasmic protein a cell surface form of nucleolin also exists. Nucleolin is expressed on the surface of MDA-MB-35 cells1 and shuttles between the cytoplasm and the nucleus and between the cell surface and the nucleus. Nucleolin is also overexpressed in 9L glioma cells. Therefore, the mechanism of F3 targeting is recognition by nucleolin at the surface of actively growing cells (tumor cells and neovascular endothelial cells), which then binds and internalizes it, and transports it into the nucleus. While nucleolin can carry F3-targeted molecules from the cell surface into the nucleus, F3-labelled PAA nanoparticles containing Photofrin accumulated in the cytoplasm, which is useful because mitochondria are the primary target of PDT-produced $1O_2$. F3 targeting has been used recently to deliver nano-sized particles composed of lipids or quantum dots to tumor vasculature.

Integrin Targeting.

Integrins are a major group of cell membrane receptors with both adhesive and signaling functions. They influence behavior of neoplastic cells by their interaction with the surrounding extracellular matrix, participating in tumor development16. Integrin $\alpha V\beta 3$ in tumor cells binds to matrix metalloprotease-2 in a proteolytically active form and facilitates cell-mediated collagen degradation and invasion. It over-expresses in U87 and 9L glioma tumors. An increase in its expression is correlated with increased malignancy in melanomas. $\alpha v\beta 3$ plays a critical role in angiogenesis and is up-regulated in vascular cells within human tumors. Significant overexpression of $\alpha v\beta 3$ is reported in colon, lung, pancreas, brain and breast carcinomas, which was significantly higher in metastatic tumors. Our objective is to prepare a known integrin $\alpha v\beta 3$-targeting ligand. While some recent work suggests that dimeric RGD peptides provide additional affinity and tumor binding, our recent in vitro data with HPPH-RGD conjugates (in one of which the binding site was blocked) shows the validity of our approach using monomeric RGD peptides.

Imaging

Optical Imaging and Tumor Detection.

Multiple, complementary techniques for tumor detection, including magnetic resonance, scintigraphic and optical imaging are under active development. Each approach has particular strengths and advantages. Optical imaging includes measurement of absorption of endogenous molecules (e.g. hemoglobin) or administered dyes, detection of bioluminescence in preclinical models, and detection of fluorescence from endogenous fluorophores or from targeted exogenous molecules. Fluorescence, the mission of absorbed light at a longer wavelength, can be highly sensitive: a typical cyanine dye with a lifetime of 0.6 nsec can emit up to 1032 photons/second/mole. A sensitive optical detector can image <103 photons/second. Thus even with low excitation power, low levels of fluorescent molecular beacons can be detected. A challenge is to deliver the dyes selectively and in high enough concentration to detect small tumors. Use of ICG alone to image hypervascular or "leaky" angiogenic vessels around tumors has been disappointing, due to its limited intrinsic tumor selectivity. Multiple approaches have been employed to improve optical probelocalization, including administering it in a quenched form that is activated within tumors, or coupling it to antibodies or small molecules such as receptor ligands. Recent studies have focused on developing dye conjugates of small bioactive molecules, to improve rapid diffusion to target tissue and use combinatorial and high throughput strategies to identify, optimize, and enhance in vivo stability of the new probes. Some peptide analogs of ICG derivatives have moderate tumor specificity and are entering pre-clinical studies. However, none of these compounds are designed for both tumor detection and therapy. It is important to develop targeting strategies that cope with the heterogeneity of tumors in vivo, where there are inconsistent and varying expressions of targetable sites.

Photosensitizers are not Optimal for Tumor Detection

Photosensitizers (PS) generally fluoresce and their fluorescence properties in vivo has been exploited for the detection of early-stage cancers in the lung, bladder and other sites 17 For treatment of early disease or for deep seated tumors the fluorescence can be used to guide the activating light. However, PS are not optimal fluorophores for tumor detection for several reasons: (i) They have low fluorescence quantum yields (especially the long wavelength photosensitizers related to bacteriochlorins). Efficient PS tend to have lower fluorescence efficiency (quantum yield) than compounds designed to be fluorophores, such as cyanine dyes because the excited singlet state energy emitted as fluorescence is instead transferred to the triplet state and then to molecular oxygen. (ii) They have small Stokes shifts. Porphyrin-based PS have a relatively small difference between the long wavelength absorption band and the fluorescence wavelength (Stokes shift), which makes it technically difficult to separate the fluorescence from the excitation wavelength. (iii) Most PS have relatively short fluorescent wavelengths, <800 nm, which are not optimal for detection deep in tissues.

Advantages and Limitations of Bifunctional Photosensitizes Fluorophore Conjugates.

In a separate study we have developed certain bifunctional conjugates that use tumor-avid PS to target the NIR fluorophores to the tumor18. The function of the fluorophore is to visualize the tumor location and treatment site. The presence of the PS allows subsequent tumor ablation. The optical imaging allows the clinician performing PDT to continuously acquire and display patient data in real-time. This "see and treat" approach may determine where to treat superficial carcinomas and how to reach deep-seated tumors in sites such as the breast, lung and brain with optical fibers delivering the photo-activating light. A similar approach was also used for developing potential PDT/MRI conjugates in which HPPH was conjugated with Gd(III)DTPA Due to a significant difference between imaging and therapeutic doses, the use of a single molecule that includes both modalities is problematic. However, with PAA NPs we were able to solve this problem.

PS-Directed PET Imaging.

Positron emission tomography (PET) is a technique that permits non-invasive use of radioisotope labeled molecular imaging probes to image and assay biochemical processes at the level of cellular function in living subjects20. PET predominately has been used as a metabolic marker, without specific targeting to malignancies. Recently, there has been growing use of radiolabeled peptide ligands to target malignancies. Currently, PET is important in clinical care and is a critical component in biomedical research, supporting a wide range of applications, including studies of gene expression, perfusion, metabolism and substrate utilization, neurotransmitters, neural activation and plasticity, receptors and antibodies, stem cell trafficking, tumor hypoxia, apoptosis and angiogenesis21. Available isotope labels include 11C (t1/2=20.4 min), 18F (t1/2=110 min), 4Cu (t1/2=12.8 h) and 124I (t1/2=4.2 days). For targeting, a long circulation time may be desirable, as it can increase delivery of the agent into tumors. HPPH and the iodobenzyl pheophorbide-a have plasma half lives ~25 h. The long radiological half life of 124I is well matched to the pheophorbides; it permits sequential imaging with time for clearance from normal tissue. Labeling techniques with radioiodine are well defined with good yield and radiochemical purity22. Despite the complex decay scheme of 124I which results in only 25% abundance of positron (compared with 100% positron emission of 18F), in vivo quantitative imaging with 124I labeled antibodies has been successfully carried out under realistic conditions using a PET/CT scanner A variety of biomolecules have been labeled with 124I. We have devised a coupling reaction which rapidly and efficiently links 124I to a tumor-avid PS23-25, and used the conjugate to target and image murine breast tumor and its metastasis to lung (See Experimental Section). Acquisition of clinical PET images can be slow, but combination PET-CT scanners allow real time guidance of therapeutic interventions. Also, new developments in tracking may permit real time interventions guided by PET data sets.

NPs can Optimize Tumor Detection and Treatment of Brain Tumors:

A photosensitizer (PS) with increased selectivity and longer wavelength could be a more suitable candidate for brain and deeply seated tumors (especially breast, brain and lung). The evolution of light sources and delivery systems is also critical to the progression of photodynamic therapy (PDT) in the medical field. Two different techniques: interstitial and intracavitary light delivery have been used for treatment of brain tumors. Powers et al26 using interstitial PDT on patients with recurrent brain tumors showed that the majority of patients had tumor recurrence within two months of treatment. However, it was later observed that treatment failures appeared to occur outside the region of the effective light treatment. Chang et al reported an effective radius of tumor cell kill in 22 glioma patients of 8 mm compared with the 1.5 cm depth of necrosis noted by Pierria with the intracavitary illumination method. It is believed that tumor resection is important so that the numbers of tumor cells remaining to treat are minimized. With stereotactic implantation of fibers for interstitial PDT there is no cavity to accommodate swelling and a considerable volume of necrotic tumor which causes cerebral edema. However, cerebral edema can be readily controlled with steroid therapy. Compared to chemotherapy and radiotherapy, patients with brain tumors treated with PDT have definitely shown long-term survival, whereas glioma patients treated with adjuvant chemotherapy or radiotherapy do not show additional benefits as reported by Kostron et al27 and Kaye et al.28 On the basis of our preliminary data, the $\alpha v\beta 3$ targeted NPs may improve tumor-selectivity and PDT outcome.

Importance of Multifunctional NPs in Brain-Tumor Imaging and PDT:

The prognosis for patients with malignant brain tumors is linked to the completeness of tumor removal. However, the borders of tumors are often indistinguishable from surrounding brain tissue so tumor excision is highly dependent upon the neurosurgeon's judgment. To identify tumors, neurosurgeons use diagnosticimaging methods such as Computed Tomography (CT) or Magnetic Resonance Imaging (MRI), which enhance the contrast between tumor and surrounding brain tissue. However, there are frequently discrepancies between intraoperative observations of tumor margins and preoperative diagnostic imaging studies. Unlike CT and MRI, intraoperative ultrasound can provide real-time information to locate the tumor and define its volume. However, once resection commences is also limited by signal artifacts caused by blood and surgical trauma limit tumor identification at the resection margin. Intraoperative MRI allows the neurosurgeon to obtain images during surgery, which can improve the completeness of the tumor resection, however microscopic disease is still not detected. In an ideal situation, the surgeon would perform the brain tumor resection with continuous guidance from high-contrast fluorescence from the tumor observed directly in the resection cavity.

BRIEF SUMMARY OF THE INVENTION

The present invention relates to polyacrylic acid (PAA) nanoparticles containing a photosensitizer and an imaging enhancing agent.

The photosensitizer is preferably a tetrapyrollic photosensitizer having the structural formula:

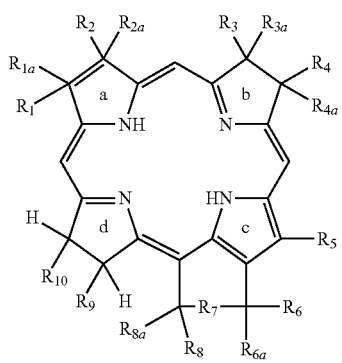

or a pharmaceutically acceptable derivative thereof, wherein:

$R_1$ and $R_2$ are each independently substituted or unsubstituted alkyl, substituted or unsubstituted alkenyl, —C(O)$R_a$ or —COO$R_a$ or —CH(CH$_3$)(O$R_a$) or —CH(CH$_3$)(O(CH$_2$)$_n$ X$R_a$) where $R_a$ is hydrogen, substituted or unsubstituted alkyl, substituted or unsubstituted alkenyl, substituted or unsubstituted alkynyl, or substituted or unsubstituted cycloalkyl; where $R_2$ may be —CH=CH$_2$, —CH(O$R_{20}$)CH$_3$, —C(O)Me, —C(=N$R_{21}$)CH$_3$ or —CH(NH$R_{21}$)CH$_3$ where X is an aryl or heteroaryl group;

n is an integer of 0 to 6;

where $R_{20}$ is methyl, butyl, heptyl, docecyl or 3,5-bis(trifluoromethyl)-benzyl; and $R_{21}$ is 3,5,-bis(trifluoromethyl)benzyl;

$R_{1a}$ and $R_{2a}$ are each independently hydrogen or substituted or unsubstituted alkyl, or together form a covalent bond;

$R_3$ and $R_4$ are each independently hydrogen or substituted or unsubstituted alkyl;

$R_{3a}$ and $R_{4a}$ are each independently hydrogen or substituted or unsubstituted alkyl, or together form a covalent bond;

$R_5$ is hydrogen or substituted or unsubstituted alkyl;

$R_6$ and $R_{6a}$ are each independently hydrogen or substituted or unsubstituted alkyl, or together form =O;

$R_7$ is a covalent bond, alkylene, azaalkyl, or azaaraalkyl or =N$R_{20}$ where $R_{20}$ is 3,5-bis(tri-fluoromethyl)benzyl or —CH$_2$X—R$^1$ or —YR$^1$ where Y is an aryl or heteroaryl group;

$R_8$ and $R_{8a}$ are each independently hydrogen or substituted or unsubstituted alkyl or together form =O;

$R_9$ and $R_{10}$ are each independently hydrogen, or substituted or unsubstituted alkyl and $R_9$ may be —CH$_2$CH$_2$COOR$^2$ where R$^2$ is an alkyl group that may optionally substituted with one or more fluorine atoms;

each of $R_1$-$R_{10}$, when substituted, is substituted with one or more substituents each independently selected from Q, where Q is alkyl, haloalkyl, halo, pseudohalo, or —COO$R_b$ where $R_b$ is hydrogen, alkyl, alkenyl, alkynyl, cycloalkyl, aryl, heteroaryl, araalkyl, or O$R_c$ where $R_c$ is hydrogen, alkyl, alkenyl, alkynyl, cycloalkyl, or aryl or CON$R_dR_e$ where $R_d$ and $R_e$ are each independently hydrogen, alkyl, alkenyl, alkynyl, cycloalkyl, or aryl, or N$R_fR_g$ where $R_f$ and $R_g$ are each independently hydrogen, alkyl, alkenyl, alkynyl, cycloalkyl, or aryl, or =N$R_h$ where $R_h$ is hydrogen, alkyl, alkenyl, alkynyl, cycloalkyl, or aryl, or is an amino acid residue;

each Q is independently unsubstituted or is substituted with one or more substituents each independently selected from $Q_1$, where $Q_1$ is alkyl, haloalkyl, halo, pseudohalo, or —COO$R_b$ where $R_b$ is hydrogen, alkyl, alkenyl, alkynyl, cycloalkyl, aryl, heteroaryl, araalkyl, or O$R_c$ where $R_c$ is hydrogen, alkyl, alkenyl, alkynyl, cycloalkyl, or aryl or CON$R_dR_e$ where $R_d$ and $R_e$ are each independently hydrogen, alkyl, alkenyl, alkynyl, cycloalkyl, or aryl, or N$R_fR_g$ where $R_f$ and $R_g$ are each independently hydrogen, alkyl, alkenyl, alkynyl, cycloalkyl, or aryl, or =N$R_h$ where $R_h$ is hydrogen, alkyl, alkenyl, alkynyl, cycloalkyl, or aryl, or is an amino acid residue.

The photosensitizer may be conjugated with an image enhancing agent prior to incorporation into the nanoparticle, after incorporation into the nanoparticle or the photosensitizer and/or image enhancing agent may chemically bound to the nano particle and/or one or more of the photosensitizer and image enhancing agent may be physically bound to the nanoparticle.

Imaging enhancing agents may be for essentially any imaging process, e.g. Examples of such imaging enhancing agents are discussed in the background of the invention previously discussed and in the list of references incorporated by reference herein as background art.

It is to be understood that other agents may be incorporated into the nanoparticle such as tumor targeting moieties and tumor inhibiting or tumor toxic moieties.

BRIEF DESCRIPTION OF THE SEVERAL VIEWS OF THE DRAWINGS

As used herein "Figure" and "Fig." are used interchangeably.

Whole body imaging by PET. A high accumulation of the 124I-photosensitizer in tumor is clearly observed without any significant accumulation in lungs (injected dose: 100 µCi). T=Tumor, PT=Primary tumor; MT=Metastatic tumor.

Figure 7:
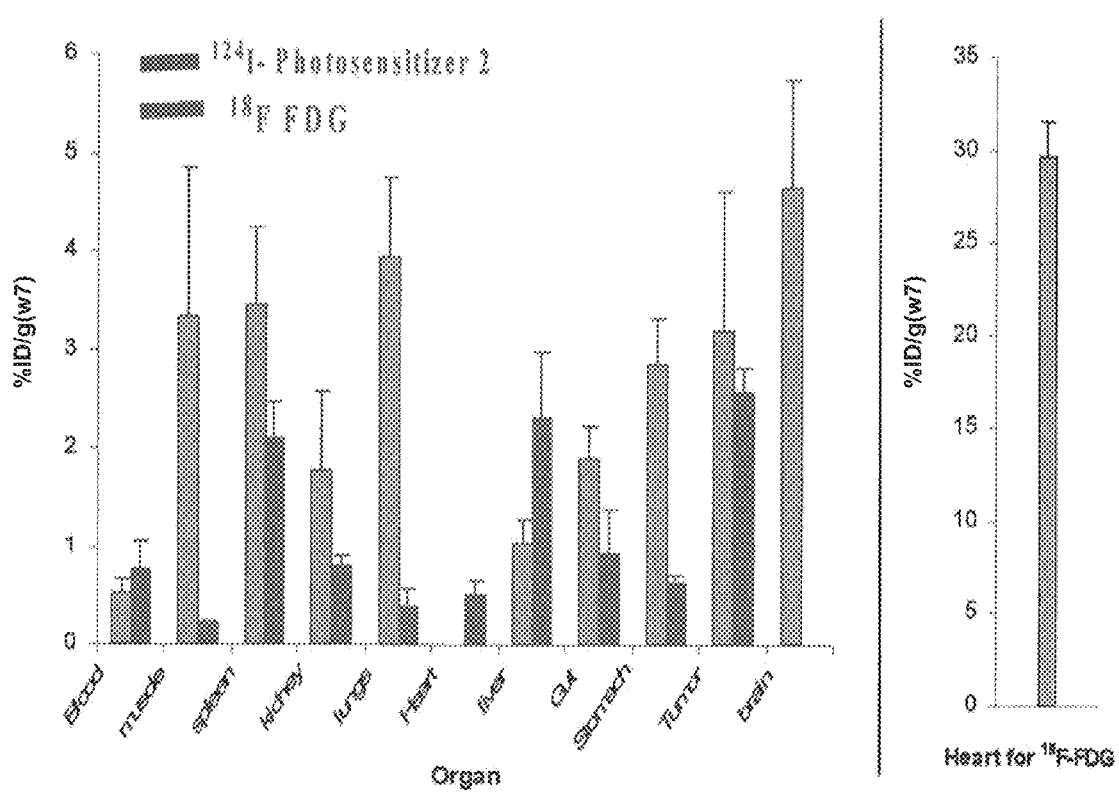

FIG. 7. In vivo biodistribution of 18F-FDG (100 µCi, half-life 2 h) at 110 min and 124I-PS 2 (100 µCi, half-life 4.2 d) at 48 h in BALB/c mice bearing Colon 26 tumor (3 mice/group). Tumor-uptake was similar for both agents. However, the higher uptake of FDG over 124I-PS 2 in normal organs is clearly evident.

Figure 8A:
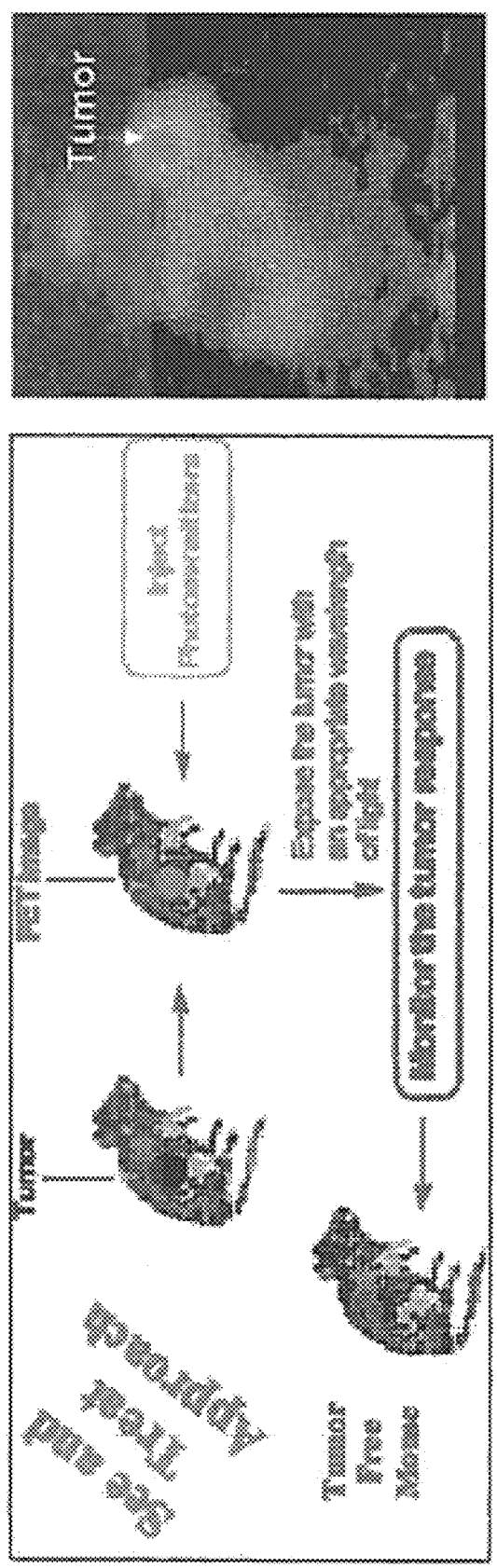

FIG. 8A. shows in vivo PET imaging (72 h post injection) and biodistribution (24 h, 48 h and 72 h postinjection) of 124I-labeled photosensitizer 2 without PAA nanoparticles in BALB/c mice bearing Colon26 tumors (see the text). [Biodistribution of PET imaging agent 2: No PAA, with PAA].

Figure 8B:
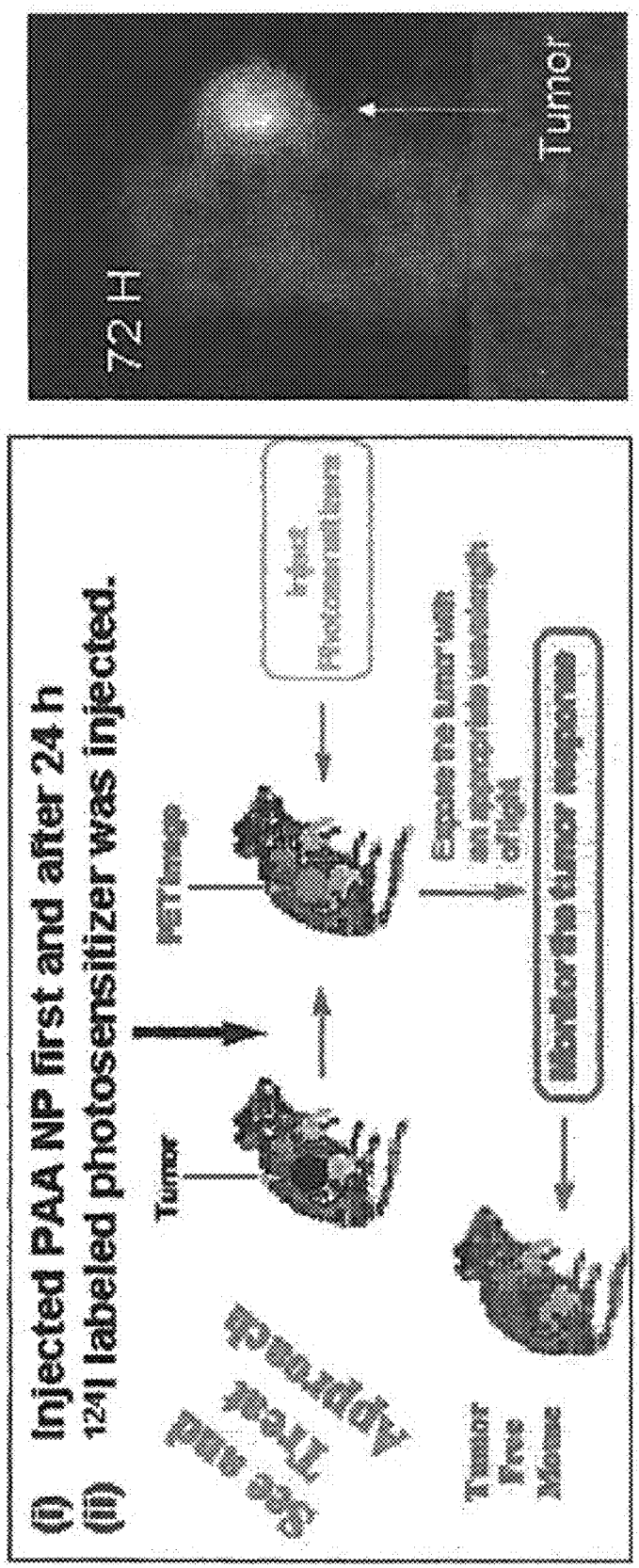

FIG. 8B shows in vivo PET imaging (72 h post injection) and biodistribution (24 h, 48 h and 72 h postinjection) of 124I-labeled photosensitizer 2 with PAA nanoparticles in BALB/c mice bearing Colon26 tumors (see the text).

Figure 8C:
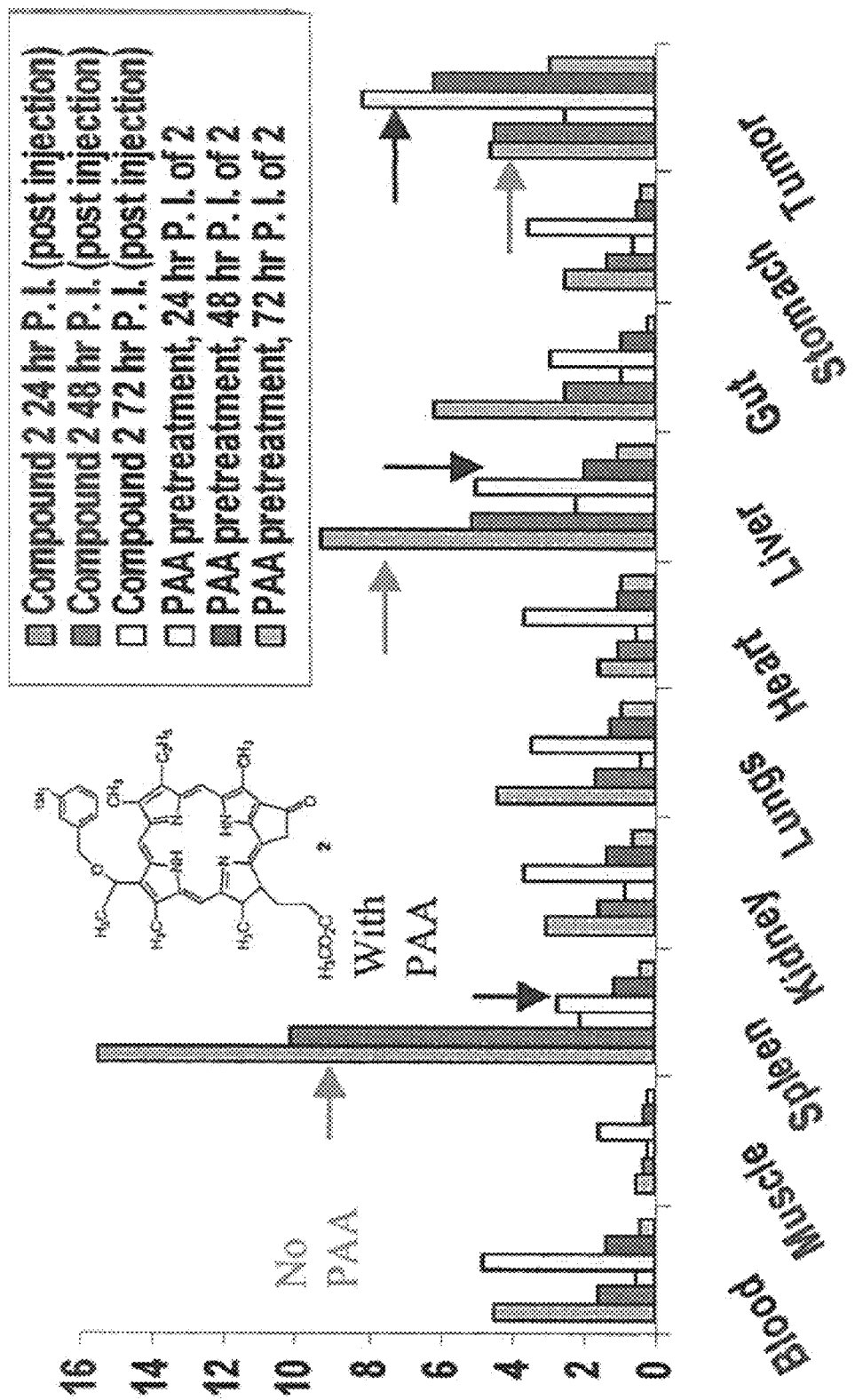

FIG. 8C shows Biodistribution of PET imaging agent 2: No PAA and with PAA

Figure 9:
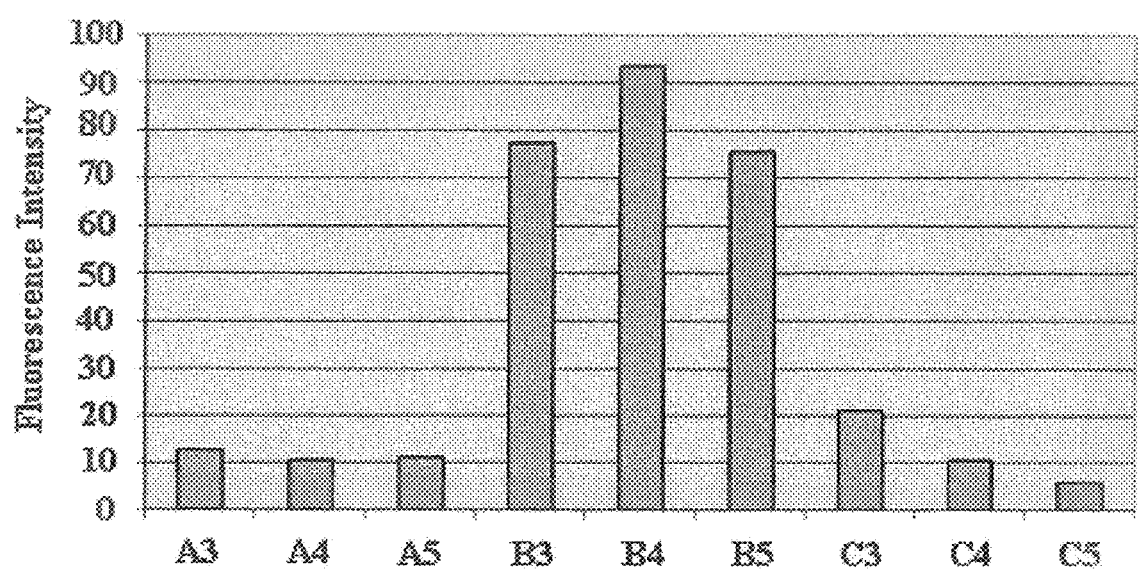

FIG. 9. Fluorescence intensity of cells targeted by F3-targeted (A series), F3-Cys targeted (B series) and nontargeted NPs (F series) in nucleolin rich MDA-MB-435 cell lines.

Figure 10:
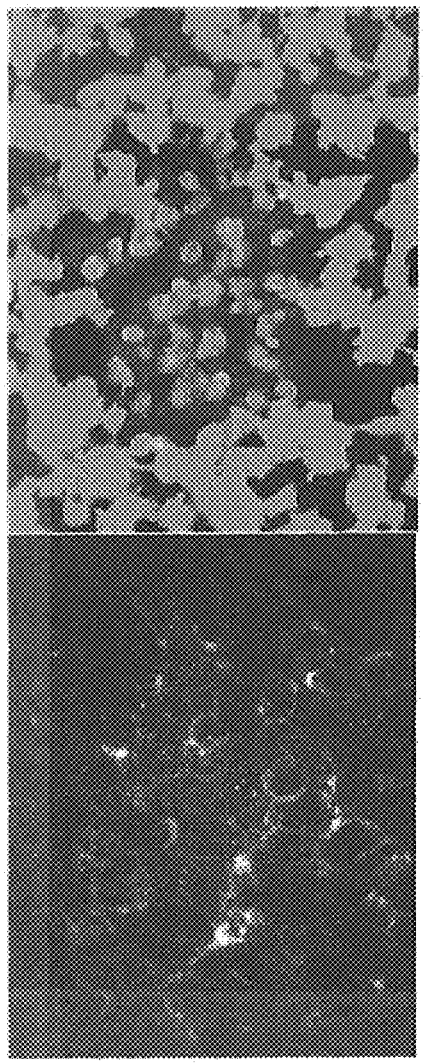
Figure 10:
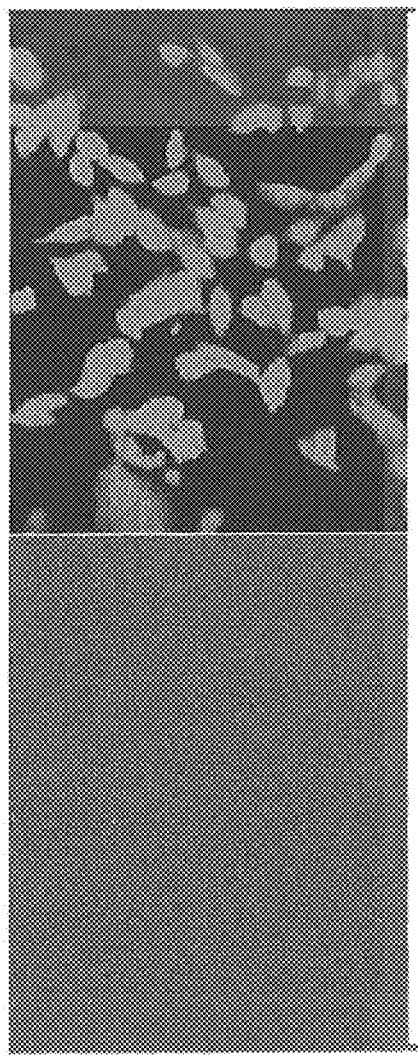

FIG. 10. Fluorescence (left) & Live/dead cell assay (right) of HPPH conjugated PAA NPs + or − F3-Cys peptide incubated for 15 min with MDA-MB-435 cells.

Figure 11:
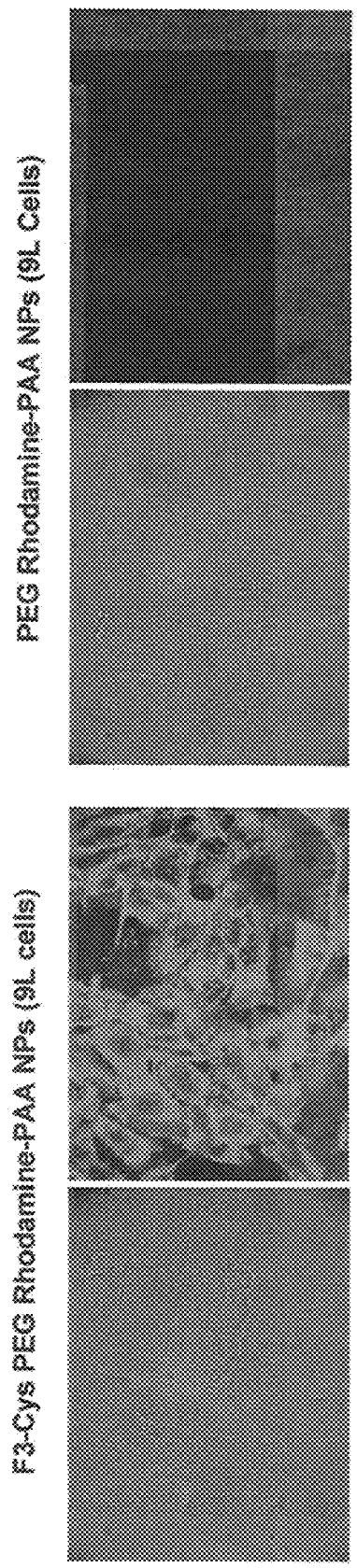

FIG. 11. Confocal images showing the target-specificity of F3-Cys peptide in 9L Glioma tumor cells. Left: F3-Cys PEG Rhodamine-PAA NPs (9L cells). Right: PEG Rhodamine-PAA NPs (9L Cells)

Figure 12:
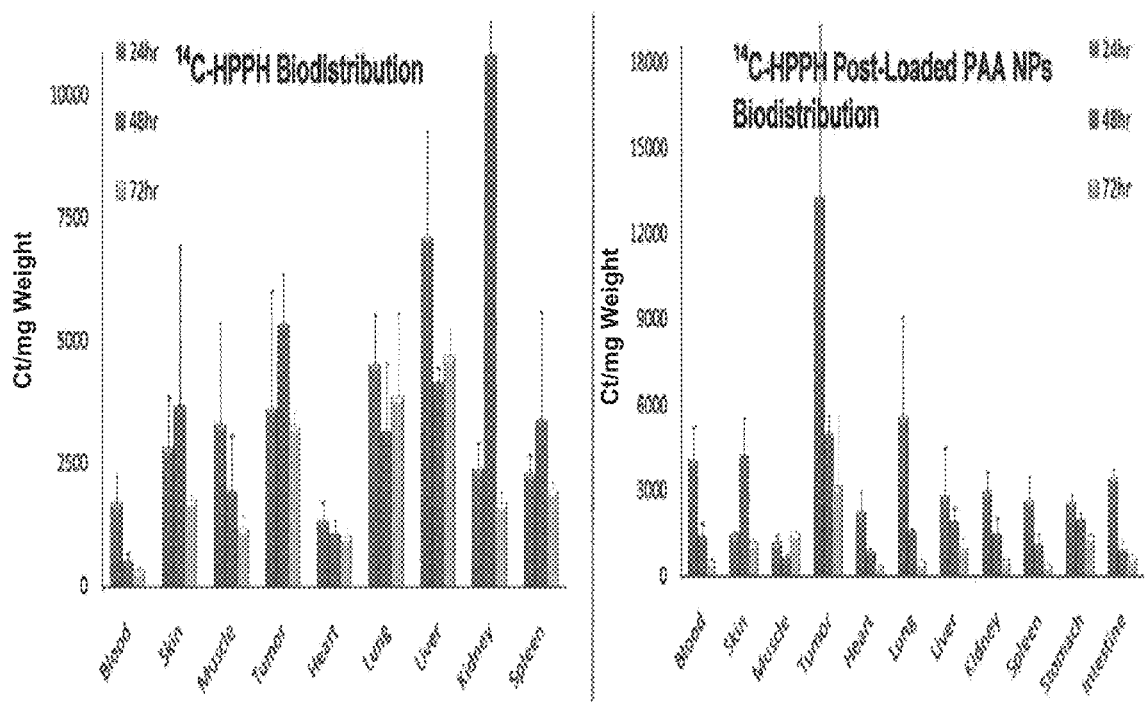

FIG. 12. In vivo biodistribution of $^{14}$C-labeled HPPH, and $^{14}$C-labeled HPPH post-loaded into PAA NPs in BALB/c mice bearing Colon26 tumors. $^{13}$C-labeled PS (3.8 µCi/0.2 mL) were administered to 12 mice/group. At 24, 48, 72 h after. injection, three mice/time-point were sacrificed. The organs of interest were removed and the radioactivity was measured The raw data were converted to counts/gram of tissue.

Figure 13A:
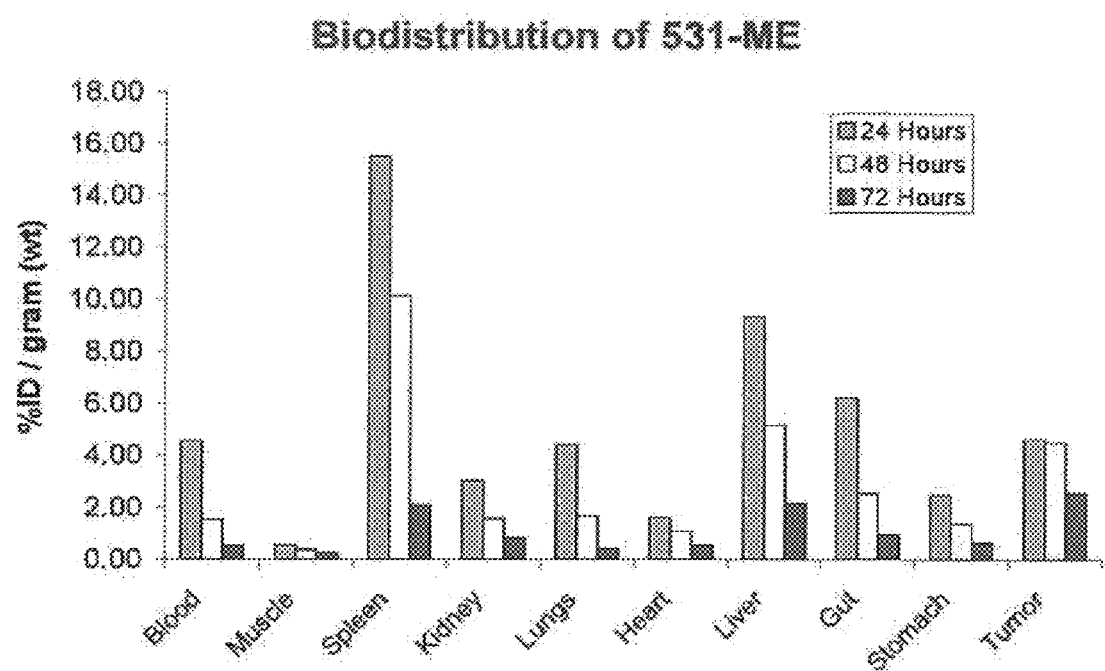

FIG. 13A. In vivo biodistribution of iodinated photosensitizer 531ME at 24, 48 and 72 h post injection.

Figure 13B:
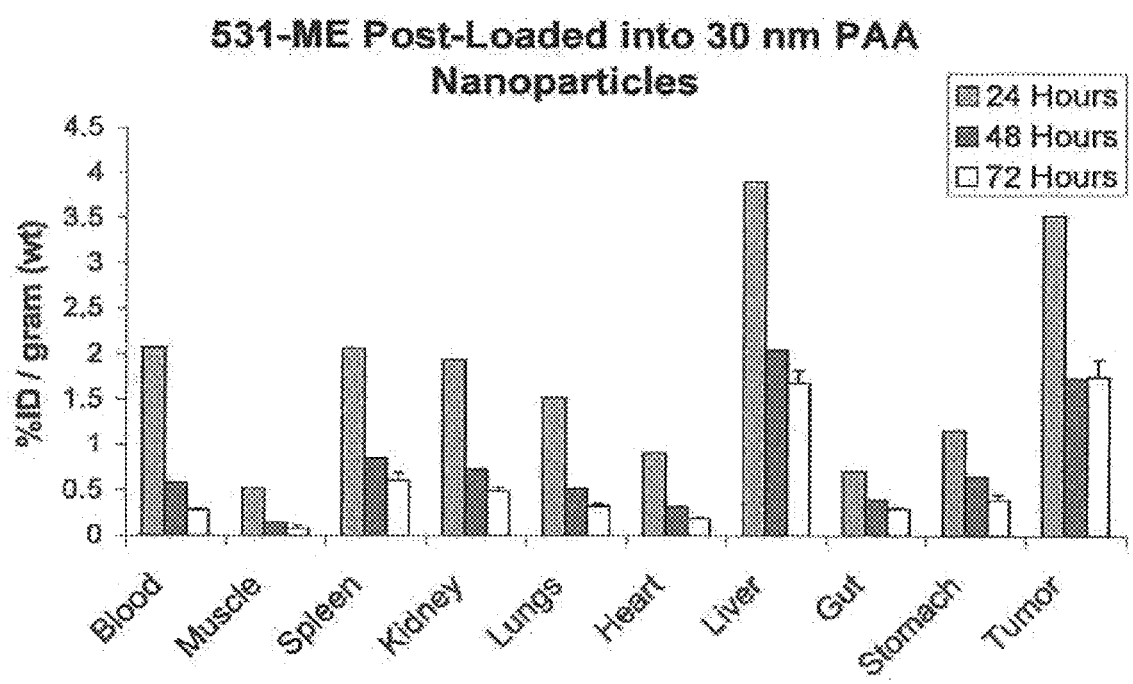

FIG. 13B In vivo biodistribution of iodinated photosensitizer of PAA NPs at 24, 48 and 72 h post injection. 531-ME Post-Loaded into 30 nm PAA Nanoparticles.

Figure 13C:
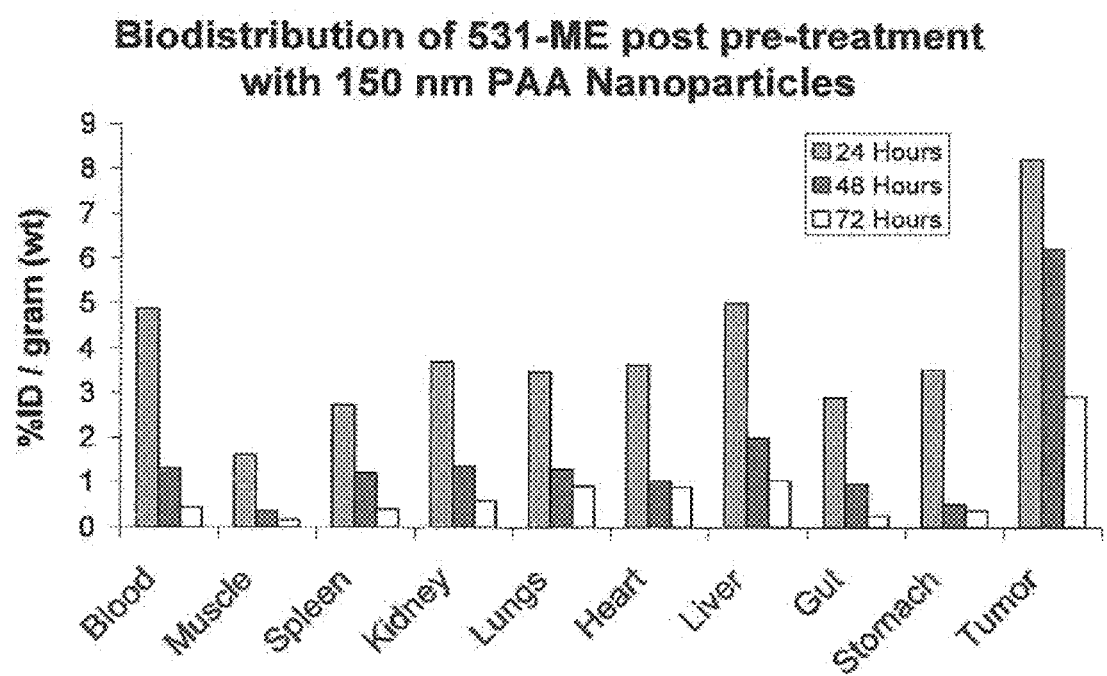

FIG. 13C In vivo biodistribution of iodinated photosensitizer of PAA NPs at 24, 48 and 72 h post injection. 531-ME post pre-treatment with 150 nm PAA Nanoparticles.

Figure 14:
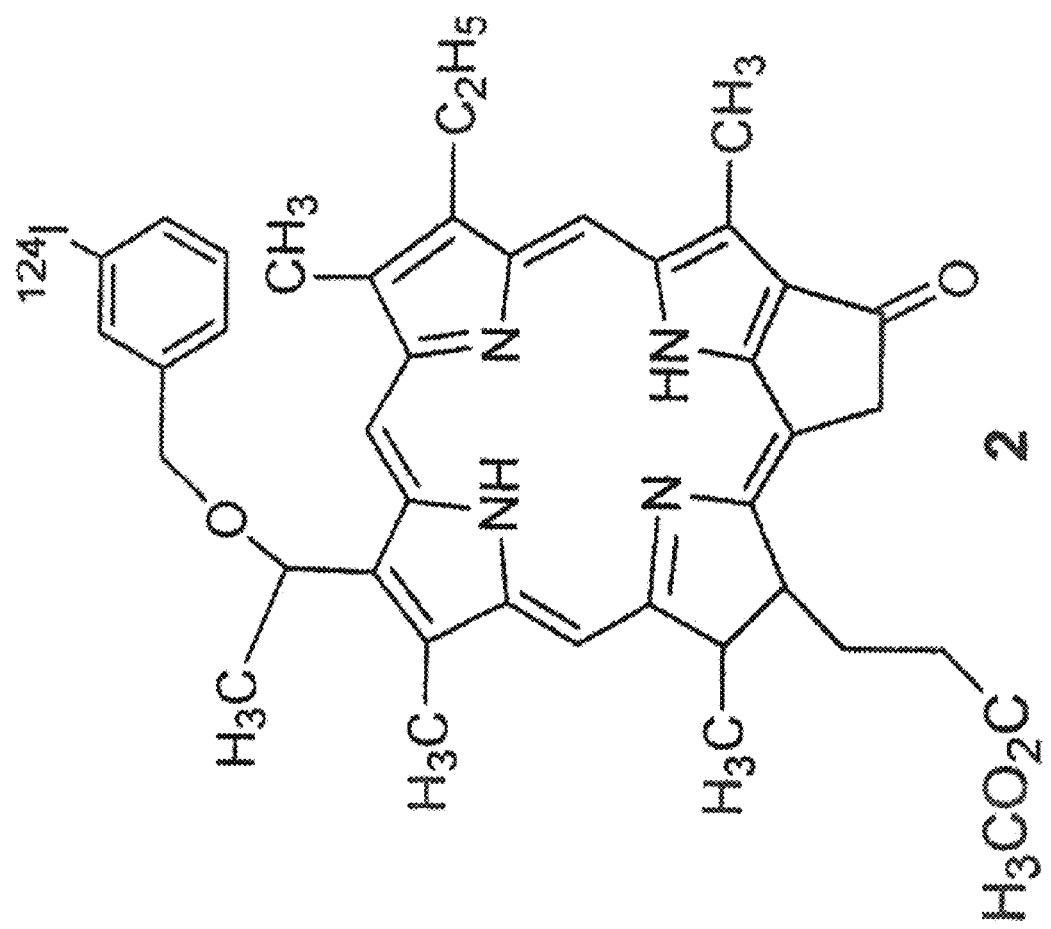

FIG. 14 shows the structural formula of HPPH.

Figure 15:
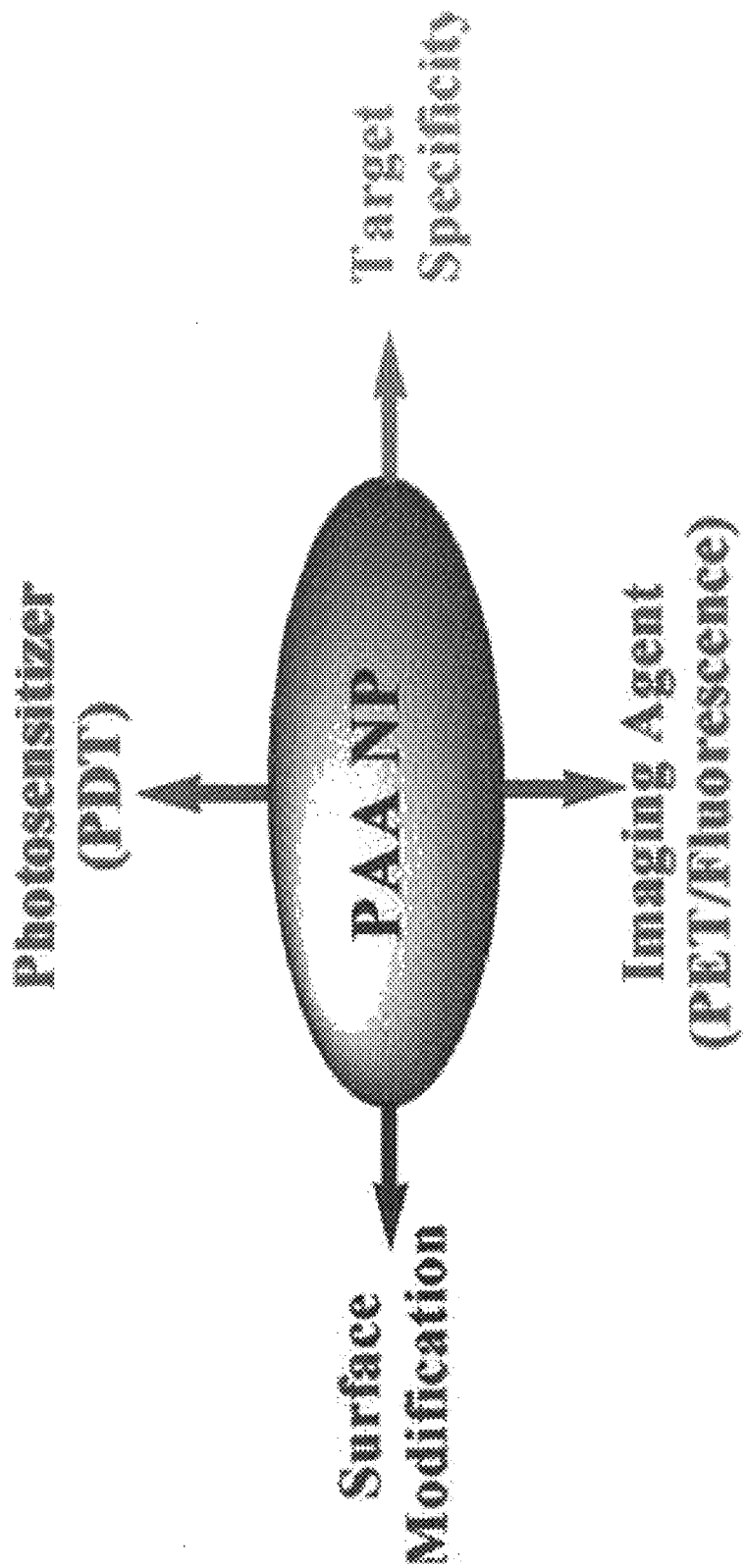

FIG. 15 is a diagram of Multifunctional PAA Nanoparticles.

Figure 16:
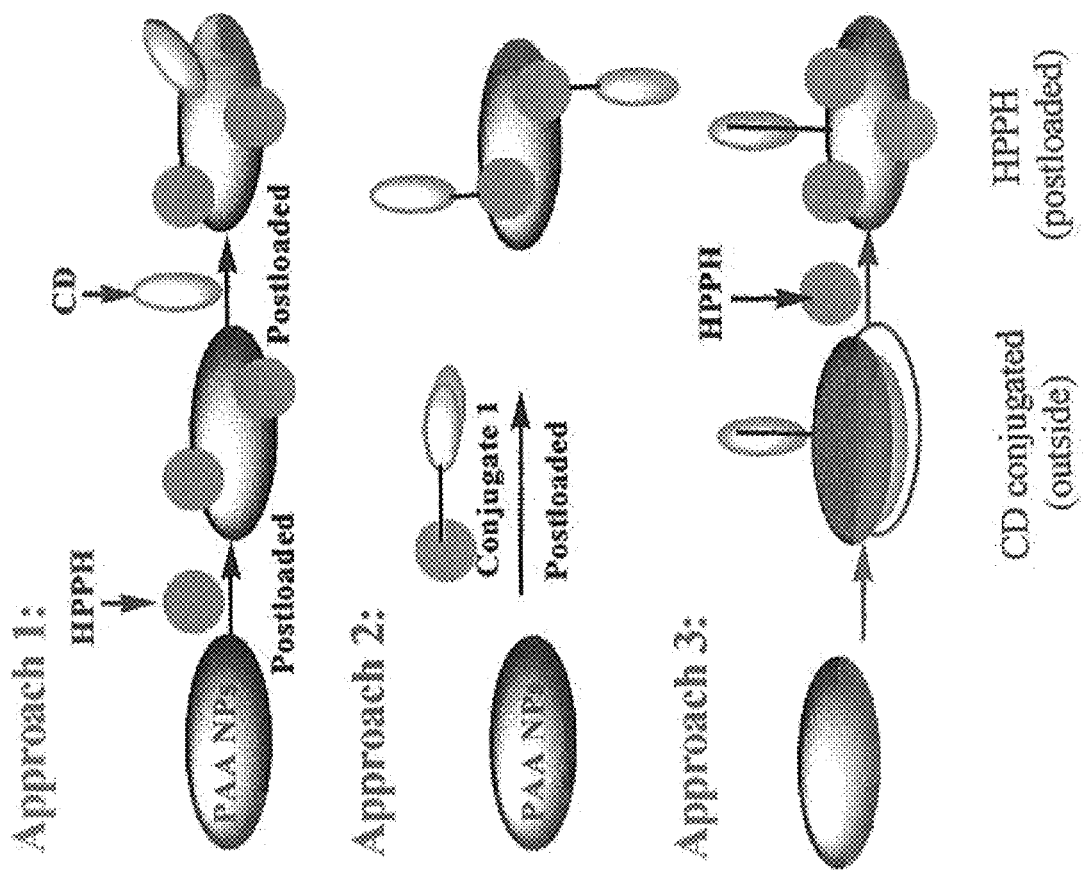

FIG. 16 shows flow diagrams for preparation of preparation of postloaded nanoparticles.

DETAILED DESCRIPTION OF THE INVENTION

Figure 1A:
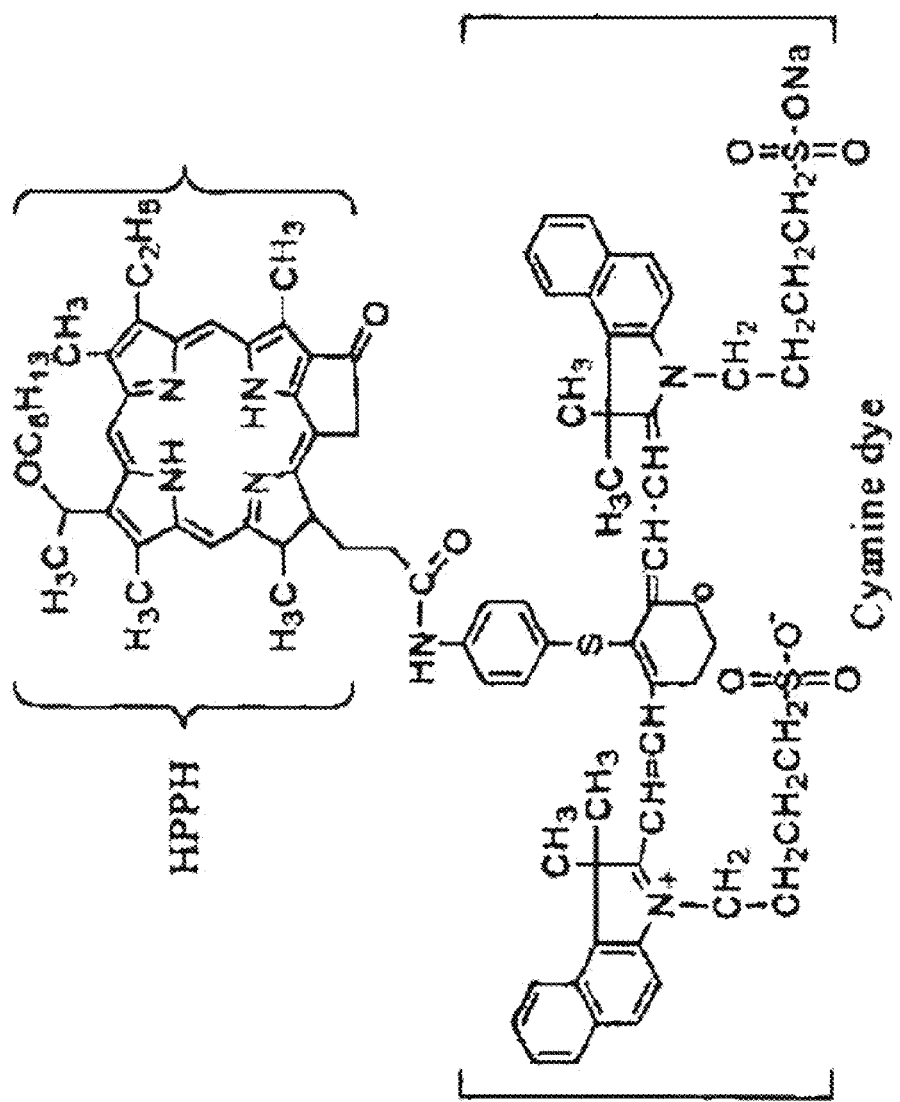
FIG. 1A shows the structural formula of HPPH-CD (cyanine dye) conjugate 1 used as a photosensitizer and imaging agent.
Figure 1B:
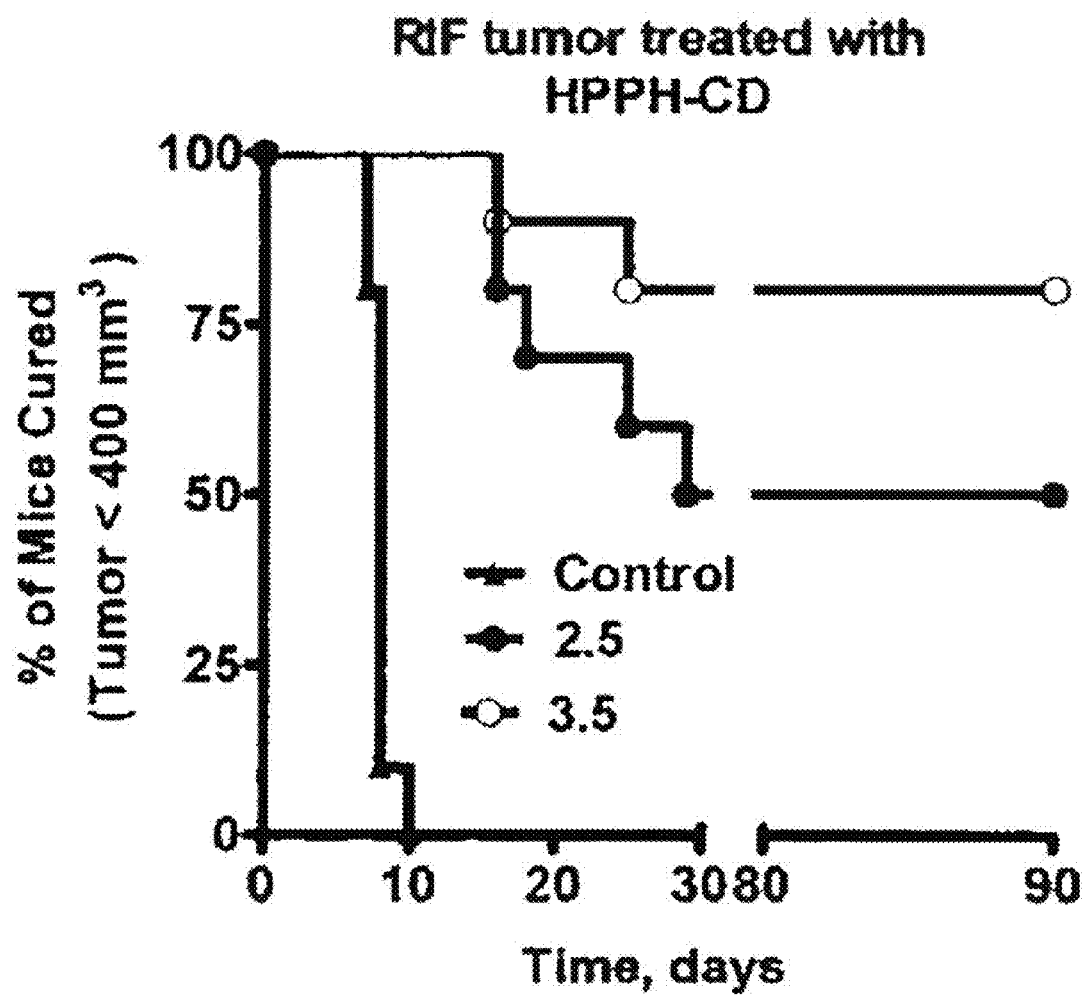
FIG. 1B: Is a graph showing In vivo photosensitizing efficacy of HPPH-CD conjugate 1 in C3H mice bearing RIF tumors (10 mice/group) at variable drug doses. The tumors were exposed to light (135 J/cm2/75 mW/cm2) at 24 h post-injection.
Figure 1C:
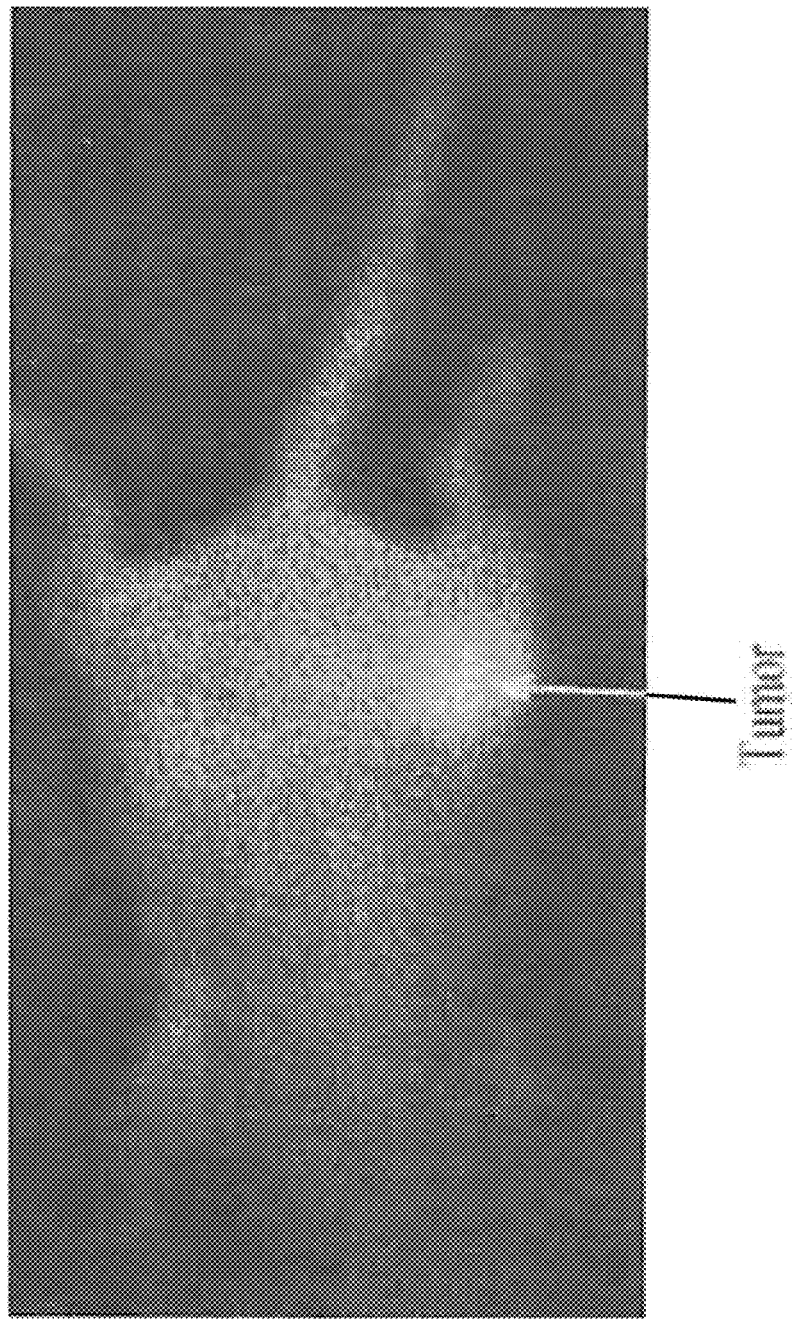
FIG. 1C shows a scanned image showing localization of the conjugate 1 in a live mouse 24 h after injection (drug dose 0.3 μmole/kg). The light treatment parameters are not optimized (in progress) [Without PAA NP]

Application of HPPH, a tumor-avid photosensitizer for developing bifunctional agents for fluorescence imaging/PDT and its limitations:

We have previously shown that certain tumor-avid PS(s) (e.g., HPPH) conjugated with NIR absorbing fluorophore(s) (non-tumor specific cyanine dyes) can be used as bifunctional agents for tumor-imaging by fuorescence and phototherapy (PDT). Here, HPPH was used as a vehicle to deliver the imaging agent to tumor. The limitation of this approach was that the conjugate exhibited significantly different dose requirements for the two modalities. The imaging dose was approximately 10-fold lower than the phototherapeutic dose (FIGS. 1B and 1C), which could be due to a part of the 1O2 (a key cytotoxic agent responsible for the destruction of the tumors) produced on exciting the PS being quenched by the fluorophore leading to its photo-destruction. Exposing the tumor at 780 nm (excitation wavelength for the cyanine dye) produced in vivo emission at 860 nm and, as expected, no significant photobleaching of the fluorophore (CD) or the PS(HPPH) was observed.

Advantages of PAA NPs for Developing Fluorescence-Imaging/PDT Agents:

For investigating the utility of PAA NPs three different approaches were used.

Figure 2:
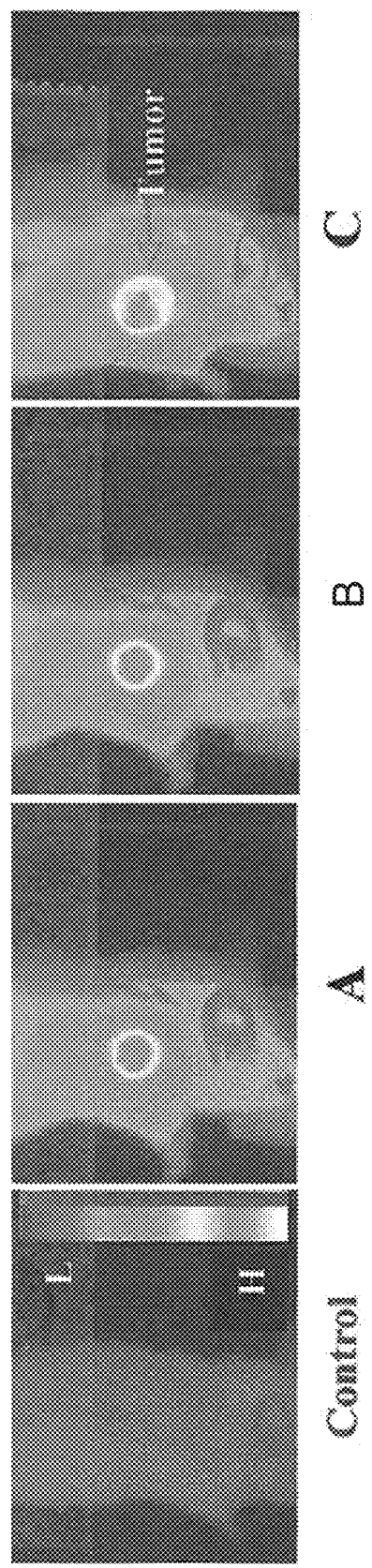
FIG. 2. Shows whole body images of BALB/c mice bearing Colon26 tumors with PAA NPs formulations (HPPH and cyanine dye (CD) were post-loaded in 2 to 1 ratio). The CD concentration was kept constant (0.3 μmol/kg) at the images were obtained at variable time points. A=24 h, B=48 h and C=72 h post injection (λex: 785 nm; λEm: 830 nm). L=Low and H=High.
Figure 3:
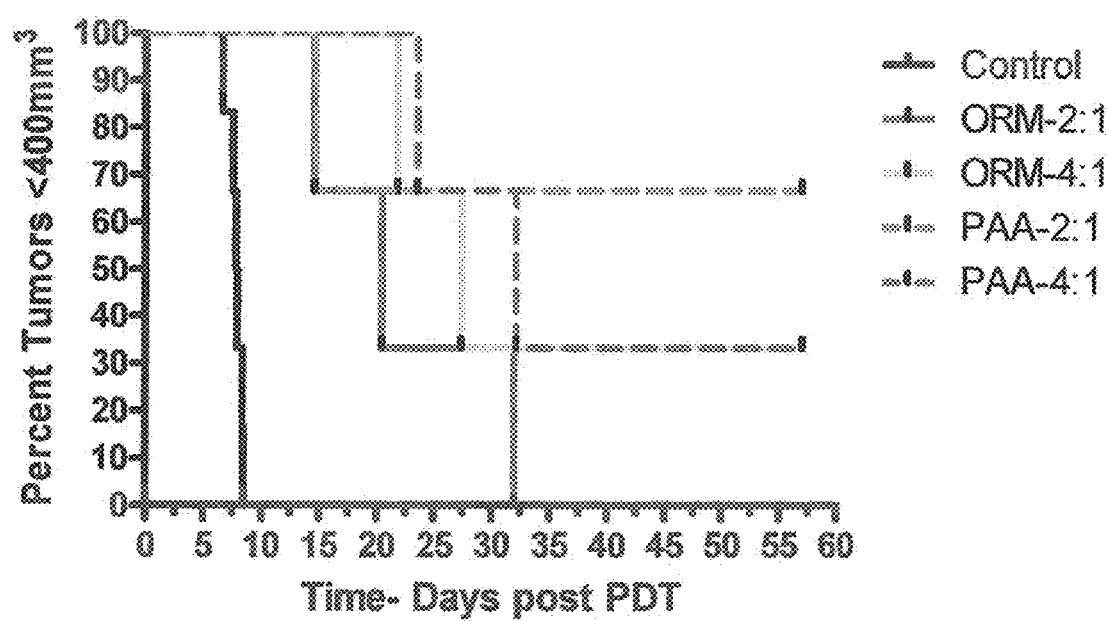
FIG. 3. Is a graph showing In vivo PDT efficacy of HPPH and CD post loaded in a ratio of 2:1 and 4:1 in PAA and ORMOSIL NPs. Note: HPPH dose: 0.47 μmol/kg in PAA NPs and 0.78 μmol/kg in ORMOSIL NPs.
Figure 4:
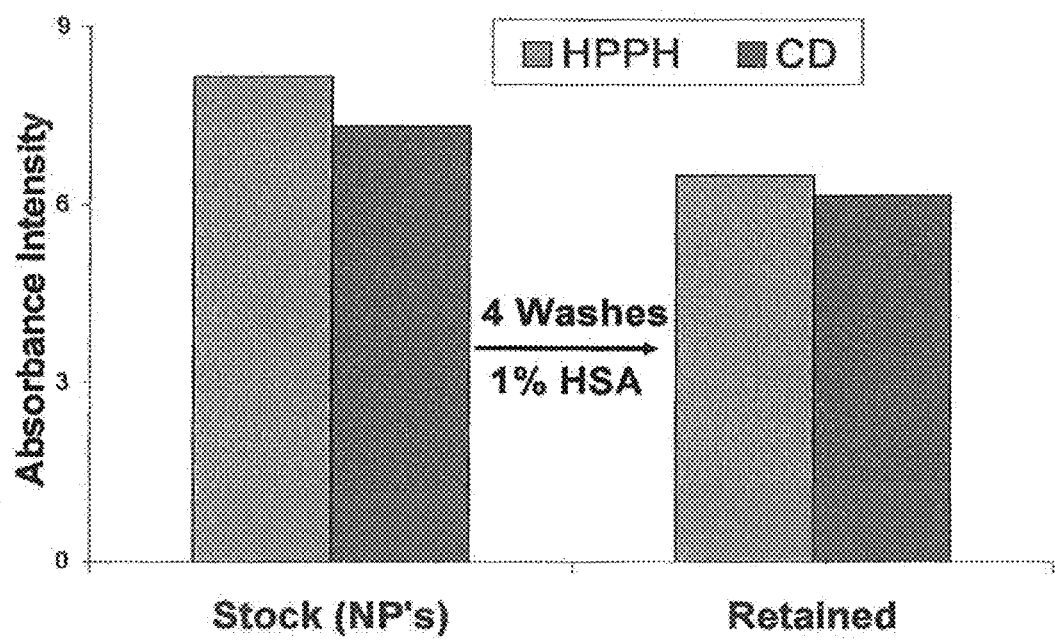
FIG. 4. Slow release of HPPH and CD from PAA NPs (post loaded in 2:1 ratio) after several washes with 1% HSA.
Figure 5A:
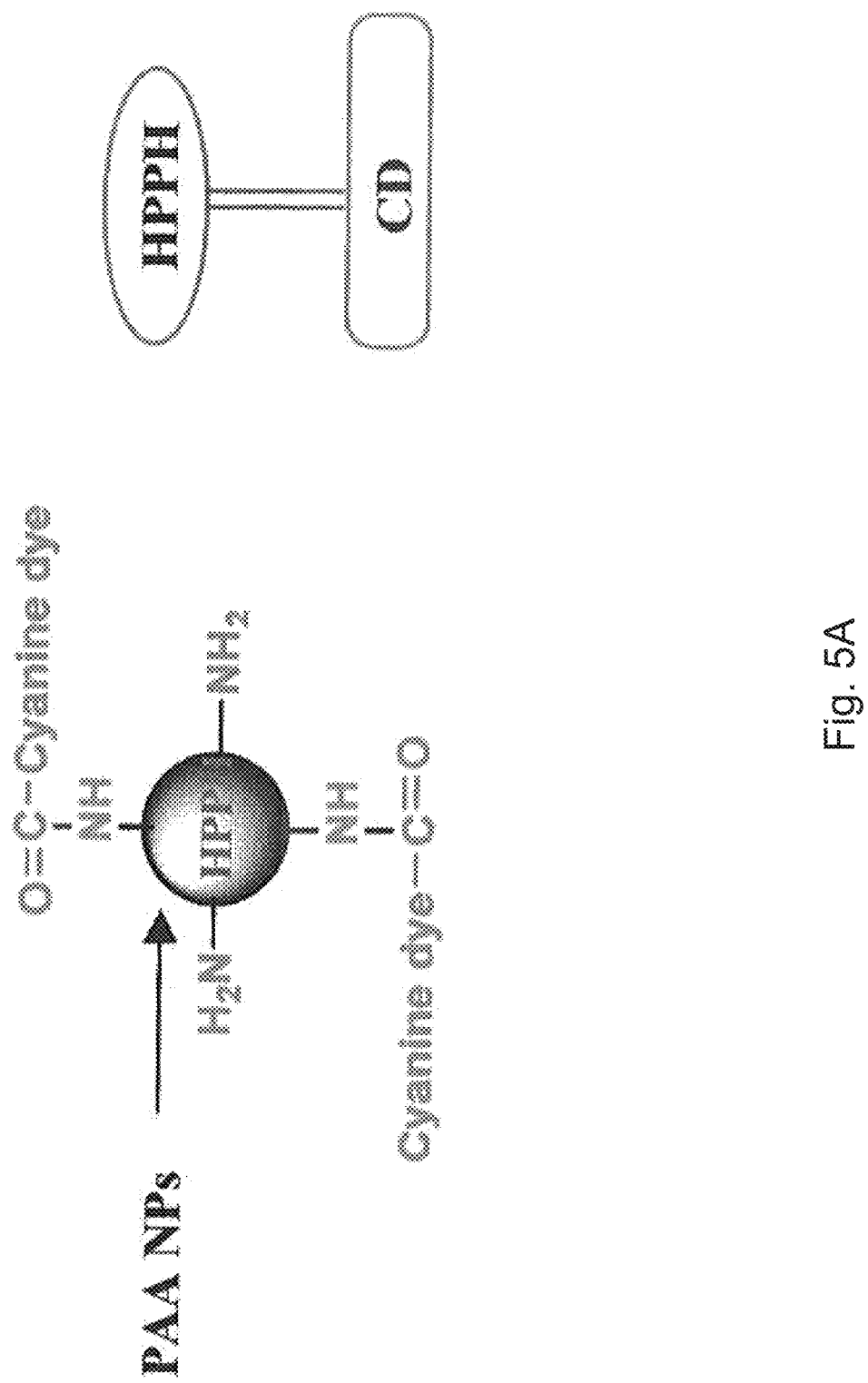
FIG. 5A is a diagram showing structure of PAA nanoparticles (PAA NP's)
Figure 5B:
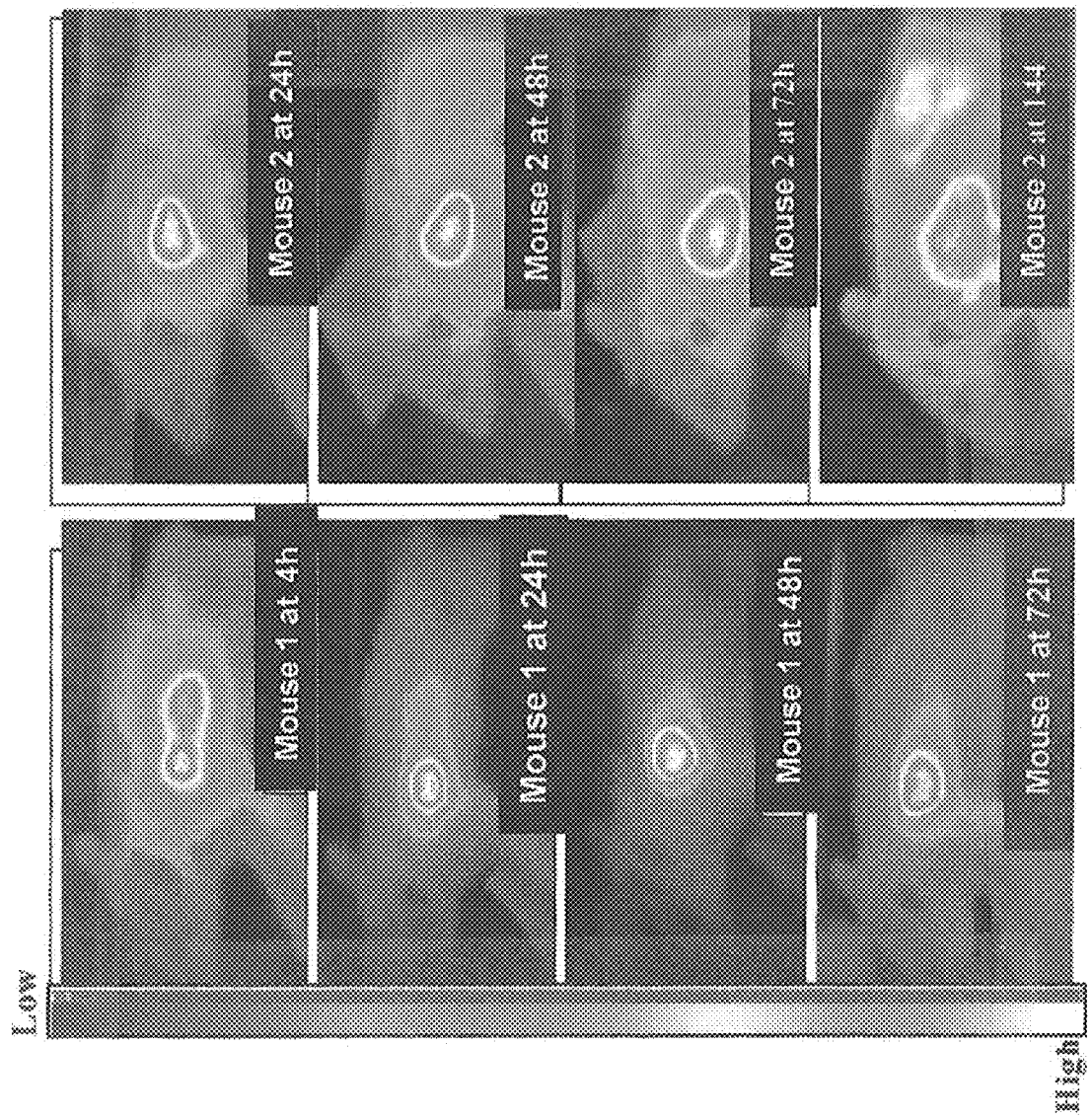
FIG. 5B. Shows comparative in vivo imaging at variable time points of BALB/c mice bearing Colon26 tumors with HPPH-CD conjugate 1 and CD-conjugated with PAA NPs/post;-loaded with HPPH. The NPs were more tumor specific. (Mouse 1)

First HPPH and the cyanine dye (fluorophore) were post-loaded in variable ratios (HPPH to CD: 1:1; 2:1; 3:1 and 4:1 molar concentrations). In brief, HPPH was postloaded to PAA NPs first. Free HPPH was removed by spin filtration and then cyanine dye was postloaded. It was spin-filtered again, washed several times with 1% bovine calf serum and the concentration was measured. The 2:1 formulations produce the best tumor imaging and long-term tumor cure in BALB/c mice bearing Colon26 tumors. This formulation contained in a single dose the therapeutic dose of HPPH (0.47 µmol/kg) and the imaging dose of Cyanine dye (0.27 mol/kg), which were similar to the components used alone for tumor imaging and therapy, but with much more tumor selectivity (skin to tumor ratio of HPPH was 4:1 instead of 2:1 without NPs). Under similar treatment parameters the Ormosil NPs showed a significantly reduced response (imaging and PDT, not shown). The stability of the drugs in PAA NP was established by repeated washing with aqueous bovine calf serum through Amicon centrifugal filter units with a 100 KDa or larger cut off membrane and drug in the filtrate was measured spectrophotometrically. The comparative in vivo PDT efficacy of the ORMOSIL and PAA formulations, their tumor imaging potential and stability (in vitro release kinetics) is shown in FIGS. 2-4, which clearly illustrate the advantages of PAA NPs in reducing the therapeutic dose by almost 8-fold without diminishing the tumor-imaging potential and also avoiding the Tween-80 formulation required for the HPPH-CD conjugate 1. In the $2^{nd}$ approach the HPPH CD conjugate 1 was post-loaded to PAA NPs, which certainly enhanced the tumor imaging, but the therapeutic dose was still 10-fold higher (similar to the HPPH CD conjugate, FIG. 5B). In the 3rd approach the cyanine dye was conjugated peripherally to the PAA NPs first and then HPPH was post loaded. Again, compared to HPPH-CD conjugate 1, the PAA formulation showed enhanced tumor-specificity (imaging) (FIG. 5B).

Figure 6:
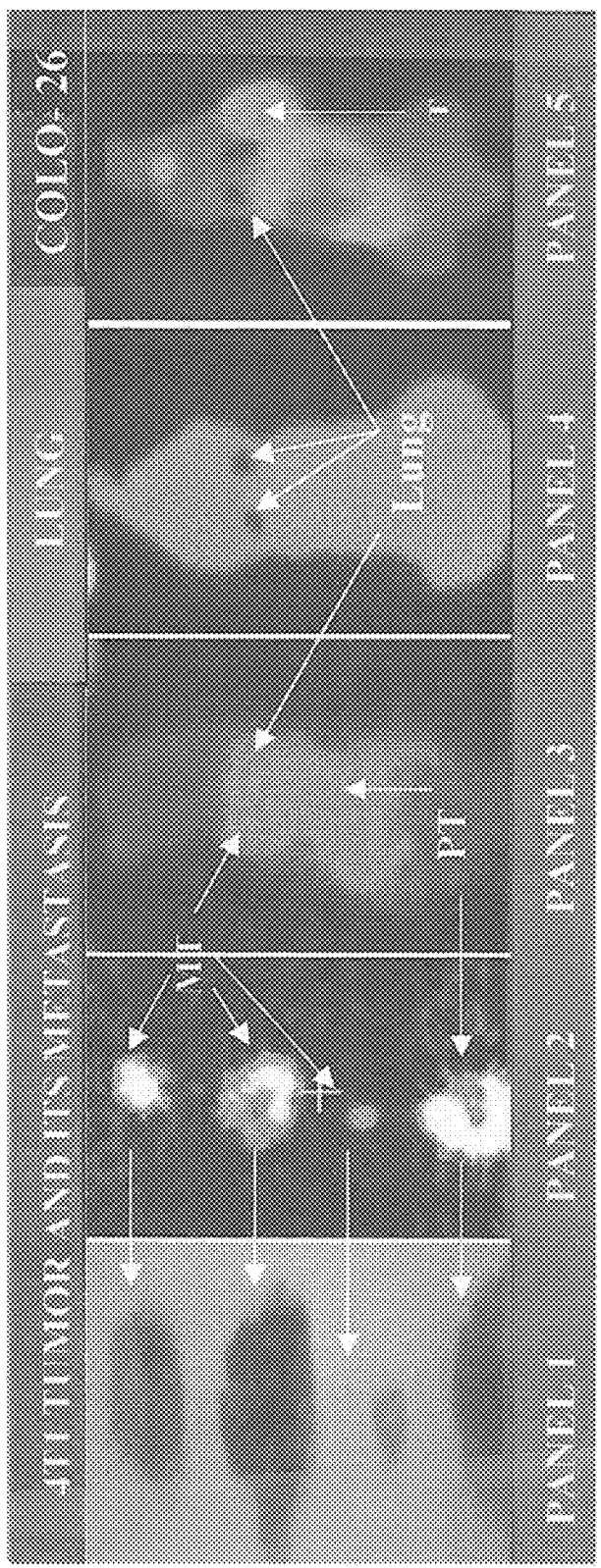
FIG. 6. shows a series of scans wherein in Panel 1 shows: (4T1 tumors): Primary (PT) and metastasized tumors (MT) dissected. Panel 2 (4T1 tumors): PET imaging of the dissected primary and metastasized tumors. Panel 3 (BALB/C mouse bearing 4T1 tumor): Whole body PET imaging. The tumor metastasis in lung was clearly observed. Panel 4: The position of the lung is shown by the transmission scan using 57Co source in mice with no lung metastasis. Panel 5: (BALB/C mouse bearing Colo-26 (non-metastatic tumor)

PET Imaging and PDT: PAA NPs Decreased the Liver Uptake of the 124I-Photosensitizes (Pet Imaging Agent) and Enhanced the Tumor-Specificity Our initial investigation with an 124I-labeled PS 2 indicates its in vivo PDT efficacy and capability of detecting tumors104-106 (RIF, Colon26, U87, GL261, pancreatic tumor xenograft)) and tumor metastases (BALB/c mice bearing orthotopic 4T1 (breast) tumors) (FIG. 6). Interestingly, compared to 18F FDG PS 2 showed enhanced contrast in most of the tumors including those where 18F FDG-PET provides limited imaging potential (e.g., brain, lung and pancreatic tumors). See FIG. 7 for comparative biodistribution. This is the first report showing the utility of porphyrin-based compounds as a "BIFUNCTIONAL AGENT" for imaging breast tumor and tumor metastasis. Similar to most NPs, PAA NP accumulate in liver and spleen. Their clearance rate from most organs is significantly faster than Ormosil NP and they do not show long-term organ toxicity. Even tumor-avid porphyrinbased PS exhibit high uptake in liver and spleen, but are non-toxic until exposed to light. The PS clear from the system quickly (days) without organ toxicity. However, radioactive PS such as the 124I-labeled analog 2 (superior to 18F-FDG in PET-imaging of lung, brain, breast and pancreas tumors) with a T1/2 of 4.2 days could cause radiation damage to normal organs. Based on the observation of high uptake of PAA NPs in liver and spleen (below) we postulated that saturating the organs with the non-toxic PAA NPs before injecting the PET agent might reduce uptake and radiation damage by 124I-imaging agent. For proof-of principle blank PAA NPs were first injected (i.v.) into mice bearing Colon26 tumors followed 24 h later by i.v. 124I-analog (100–50 μCi). The mice were imaged at 24, 48 and 72 h post injection and biodistribution studies were performed at each time point summarized in FIGS. 8A-8C (only 72 h images shown).

The presence of PAA NPs made a remarkable difference in tumor contrast with brain, lung and pancreatic tumors). See FIG. 7 for comparative biodistribution.

PAA NPs can be Targeted to Nucleolin with F3-Cys:

F3-targeted NPs were prepared using two kinds of F3 peptides: F3 peptide conjugated to NP via one of the 8 lysines available in its sequence and F3-Cys peptide conjugated to NP via cysteine. Cysteine capped NPs served as non-targeted control. Three 25 mg batches of each type of NP contained: 2.6, 5.1 and 7.7 mg F3, (A3-A5) respectively; 2.7, 5.3 and 8 mg F3-Cys (B3-B5) respectively, and 0.29, 0.58 and 0.87 mg Cys (C3-C5) respectively. The fluorescence intensity from PAA NP incubated in vitro with nucleolin positive MDA-MB-435 cells is shown in FIG. 9. The F3-Cys conjugated NPs show considerably higher binding efficiency than non-targeted NPs, while F3 conjugated NPs do not. Conjugation via a cysteine link preserves the specificity of F3 peptide for nucleolin. In addition excess cysteine on the NPs helps to minimize the non-specific binding. Additional experiments (not shown) suggested that the amount of F3-Cys peptide (5.3 mg/25 mg NP) used for B4 NPs was optimal.

Optical Properties of Post-Loaded PAA NPs.

The absorption spectrum of PAA NPs post-loaded with both HPPH and cyanine dye (even at 0.5 mg/ml), clearly shows characteristic signatures for both the PS and dye, without aggregation-induced broadening, while the fluorescence spectrum shows strong signals from both components.

HPPH Conjugated PAA NPs with F3-Cys Peptide at the Outer Surface Show Targeted Specificity:

F3-mediated specificity is retained in the presence of conjugated HPPH. F3 targeted NPs did targeted NPs did not, indicating that F3-mediated specificity is retained in the presence of conjugated HPPH. F3 targeted NPs did not accumulate in the nucleus. On activation of cells with light at 660 nm only F3-targeted NP caused cell kill (FIG. 11). Cell internalization of F3-targeted NPs was confirmed by fluorescence confocal microscopy.

HPPH Conjugated PAA NPs with F3-Cyspeptide at the Outer Surface Show Targeted Specificity:

The specificity of targeted NPs was tested by fluorescent imaging (FIG. 10). F3 targeted HPPH conjugated PAA NP specifically bound to MDA-MB-435 cells (expressing nucleolin) while non-targeted NPs did not, indicating that F3-mediated specificity is retained in the presence of conjugated HPPH. F3 targeted NPs did not accumulate in the nucleus. On activation of cells with light at 660 nm only F3-targeted NP caused cell kill (FIG. 11). Cell internalization of F3-targeted NPs was confirmed by fluorescence confocal microscopy.

F3-Cys Shows Target-Specificity in 9L Glioma Cells:

Similar to F3-cys, a pegylated form of F3-Cys PEG on PAA NPs also showed remarkable target-specificity in 9L rat glioma cells which also expresses nucleolin, FIG. 11. (Note: HPPH is replaced with a Rhodamine moiety).

Biodistribution Studies: PAA NP Enhances Tumor Uptake of HPPH:

The biodistbiodistribution of 14C-HPPH and 14C-HPPH post-loaded PAA NP was performed in BALB/c mice bearing Colon26 tumors at 24, 48 and 72 h post injection (3 mice/time point) and the results are summarized in FIG. 12. As can be seen presence of PAA NPs made a significant increase in tumor uptake with reduced uptake in other organs.

Size of PAA NPs Made Remarkable Difference in Tumor-Enhancement:

The biodistribution of 124I-photosensitizer was investigated using variable sizes of nanoparticles either injecting the NPs first and then administrating the labeled photosensitizer or postloading the labeled photosensitizer to PAA NPs and then perform in vivo biodistribution in mice at 24, 48 and 72 h. The results summarized in FIGS. 13A-13C clearly indicate that the size of PAA NPs makes a significant impact in tumor enhancement. Experiments related to in vivo PDT efficacy of these formulations are currently in progress.

This invention shows the utility of porphyrin-based compounds in a "BIFUNCTIONAL AGENT" for imaging breast tumor and tumor metastasis. Similar to most NPs, PAA NP accumulate in liver and spleen. Their clearance rate from most organs is significantly faster than Ormosil NP and they do not show long-term organ toxicity. Even tumor-avid porphyrin based PS exhibit high uptake in liver and spleen, but are non-toxic until exposed to light. The PS clear from the system quickly (days) without organ toxicity. However, radioactive PS such as the 124I-labeled analog 2 (superior to 18F-FDG in PET-imaging of lung, brain, breast and pancreas tumors) with a T1/2 of 4.2 days could cause radiation damage to normal organs. Based on the observation of high uptake of PAA NPs in liver and spleen (below) we postulated that saturating the organs with the non-toxic PAA NPs before injecting the PET agent might reduce uptake and radiation damage by 124I-imaging agent. For proof-of principle blank PAA NPs were first injected (i.v.) into mice bearing Colon26 tumors followed 24 h later by i.v. 124I-analog (100-150 μCi). The mice were imaged at 24, 48 and 72 h post injection and biodistribution studies were performed at each time point summarized in FIGS. 8A-8C (only 72 h images shown).

The presence of PAA NPs makes a remarkable difference in tumor contrast with significantly reduced uptake in spleen and liver and improved tumor-uptake/contrast at 24, 48 and 72 h post injection (3 mice/group Similar studies (tumor-imaging and PDT efficacy) in which the labeled PS is post-loaded to variable sizes. Similar studies (tumor-imaging and PDT efficacy) in which the labeled PS is post-loaded to variable sizes PAA NPs are currently in progress.

What is claimed is:

1. A composition comprising:
   PAA nanoparticles having a tetrapyrrolic photosensitizer postloaded onto the PAA nanoparticle after formation of the nanoparticle, and an imaging agent, wherein the photosensitizer is HPPH.

2. A composition comprising PAA nanoparticles containing a tetrapyrrolic photosensitizer and an imaging agent, wherein the tetrapyrrolic photosensitizer has the structural formula:

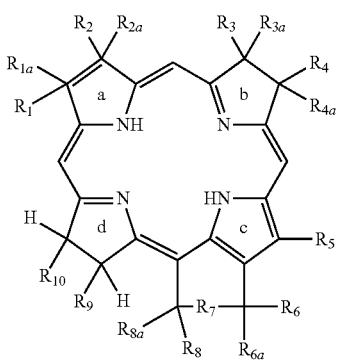

or a pharmaceutically acceptable derivative thereof, wherein:
$R_1$ and $R_2$ are each independently substituted or unsubstituted alkyl, substituted or unsubstituted alkenyl, —C(O)$R_a$ or —COOR$_a$ or —CH(CH$_3$)(OR$_a$) or —CH(CH$_3$)(O(CH$_2$)$_n$XR$_a$) where $R_a$ is hydrogen, substituted or unsubstituted alkyl, substituted or unsubstituted alkenyl, substituted or unsubstituted alkynyl, or substituted or unsubstituted cycloalkyl; where $R_2$ may be —CH=CH$_2$, —CH(OR$_{20}$)CH$_3$, —C(O)Me, —C(=NR$_{21}$)CH$_3$ or —CH(NHR$_{21}$)CH$_3$
where X is an aryl or heteroaryl group;
n is an integer of 0 to 6;
where $R_{20}$ is methyl, butyl, heptyl, docecyl or 3,5-bis(trifluoromethyl)-benzyl; and
$R_{21}$ is 3,5,-bis(trifluoromethyl)benzyl;
$R_{1a}$ and $R_{2a}$ are each independently hydrogen or substituted or unsubstituted alkyl, or together form a covalent bond;
$R_3$ and $R_4$ are each independently hydrogen or substituted or unsubstituted alkyl;
$R_{3a}$ and $R_{4a}$ are each independently hydrogen or substituted or unsubstituted alkyl, or together form a covalent bond;
$R_5$ is hydrogen or substituted or unsubstituted alkyl;
$R_6$ and $R_{6a}$ are each independently hydrogen or substituted or unsubstituted alkyl, or together form =O;
$R_7$ is a covalent bond, alkylene, azaalkyl, or azaaraalkyl or =NR$_{20}$ where R$_{20}$ is 3,5-bis(tri-fluoromethyl)benzyl or —CH$_2$X—R$^1$ or —YR$^1$ where Y is an aryl or heteroaryl group;
$R_8$ and $R_{8a}$ are each independently hydrogen or substituted or unsubstituted alkyl or together form =O;
$R_9$ and $R_{10}$ are each independently hydrogen, or substituted or unsubstituted alkyl and $R_9$ may be —CH$_2$CH$_2$COOR$^2$ where R$^2$ is an alkyl group that may optionally substituted with one or more fluorine atoms;
each of $R_1$-$R_{10}$, when substituted, is substituted with one or more substituents each independently selected from Q, where Q is alkyl, haloalkyl, halo, photosensitizereudohalo, or —COOR$_b$ where R$_b$ is hydrogen, alkyl, alkenyl, alkynyl, cycloalkyl, aryl, heteroaryl, araalkyl, or OR$_c$ where R$_c$ is hydrogen, alkyl, alkenyl, alkynyl, cycloalkyl, or aryl or CONR$_d$R$_e$ where R$_d$ and R$_e$ are each independently hydrogen, alkyl, alkenyl, alkynyl, cycloalkyl, or aryl, or NR$_f$R$_g$ where R$_f$ and R$_g$ are each independently hydrogen, alkyl, alkenyl, alkynyl, cycloalkyl, or aryl, or =NR$_h$ where R$_h$ is hydrogen, alkyl, alkenyl, alkynyl, cycloalkyl, or aryl, or is an amino acid residue;
each Q is independently unsubstituted or is substituted with one or more substituents each independently selected from Q$_1$, where Q$_1$ is alkyl, haloalkyl, halo, photosensitizereudohalo, or —COOR$_b$ where R$_b$ is hydrogen, alkyl, alkenyl, alkynyl, cycloalkyl, aryl, heteroaryl, araalkyl, or OR$_c$ where R$_c$ is hydrogen, alkyl, alkenyl, alkynyl, cycloalkyl, or aryl or CONR$_d$R$_e$ where R$_d$ and R$_e$ are each independently hydrogen, alkyl, alkenyl, alkynyl, cycloalkyl, or aryl, or NR$_f$R$_g$ where R$_f$ and R$_g$ are each independently hydrogen, alkyl, alkenyl, alkynyl, cycloalkyl, or aryl, or =NR$_h$ where R$_h$ is hydrogen, alkyl, alkenyl, alkynyl, cycloalkyl, or aryl, or is an amino acid residue.

wherein the photosensitizer is postloaded onto the nanoparticle after nanoparticle formation.

3. The composition of claim 2 wherein the imaging agent is a cyanine dye.

4. The composition of claim 3 wherein the imaging agent is a $^{124}$I labeled compound.

5. The composition of claim 2 wherein the imaging agent is a PET, fluorescence or MR imaging agent.

6. The composition of claim 5 wherein the nanoparticle contains a targeting moiety.

7. The composition of claim 6 wherein the targeting moiety is a peptide, folic acid or a carbohydrate.

* * * * *